United States Patent
Justin et al.

(10) Patent No.: US 10,568,524 B2
(45) Date of Patent: Feb. 25, 2020

(54) COMPLIANCE CHECKER FOR SERVICE AGREEMENT

(71) Applicant: INTEL CORPORATION, Santa Clara, CA (US)

(72) Inventors: Jerin C. Justin, San Jose, CA (US); Kumar Balasubramanian, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 217 days.

(21) Appl. No.: 15/638,761

(22) Filed: Jun. 30, 2017

(65) Prior Publication Data

US 2018/0062959 A1 Mar. 1, 2018

Related U.S. Application Data

(60) Provisional application No. 62/379,322, filed on Aug. 25, 2016.

(51) Int. Cl.
| | |
|---|---|
| *A61B 5/01* | (2006.01) |
| *H04L 12/24* | (2006.01) |
| *H04W 4/70* | (2018.01) |
| *H04L 12/26* | (2006.01) |
| *H04L 29/08* | (2006.01) |
| *A61B 5/024* | (2006.01) |
| *G16H 50/30* | (2018.01) |
| *A61B 5/00* | (2006.01) |
| *A61B 5/0205* | (2006.01) |

(52) U.S. Cl.
CPC ............... *A61B 5/01* (2013.01); *A61B 5/024* (2013.01); *H04L 41/5006* (2013.01); *H04L 43/08* (2013.01); *H04L 67/22* (2013.01); *H04W 4/70* (2018.02); *A61B 5/0008* (2013.01); *A61B 5/02055* (2013.01); *A61B 5/681* (2013.01); *G16H 50/30* (2018.01)

(58) Field of Classification Search
CPC ..... H04L 43/08; H04L 41/5006; H04L 67/22; H04W 4/70
USPC ......................................................... 709/224
See application file for complete search history.

(56) References Cited

U.S. PATENT DOCUMENTS

| | | | |
|---|---|---|---|
| 2012/0217978 A1* | 8/2012 | Shen ...................... | G06F 3/0418 324/601 |
| 2013/0179134 A1* | 7/2013 | Li .......................... | G01C 19/38 703/7 |
| 2014/0092753 A1 | 4/2014 | Vasseur et al. | |

(Continued)

OTHER PUBLICATIONS

Gaillard, SLA Specification for IoT Operation, Jul. 15, 2014, HAL archives-ouvertes, https://hal.inria.fr/hal-01024259/document (Year: 2014).*

(Continued)

*Primary Examiner* — Zi Ye
(74) *Attorney, Agent, or Firm* — International IP Law Group, P.L.L.C.

(57) ABSTRACT

A method and apparatus including a computing device to quantify a term of a service agreement in a context of a proposed solution, evaluate solution characteristics against a given gateway architecture, and compare the solution characteristics to desired service-agreement solution metrics. The solution characteristics include simulated observed characteristics.

25 Claims, 9 Drawing Sheets

(56) References Cited

U.S. PATENT DOCUMENTS

| | | | |
|---|---|---|---|
| 2015/0180800 A1* | 6/2015 | Vasseur | H04L 47/10 |
| | | | 370/236 |
| 2015/0319076 A1 | 11/2015 | Vasseur et al. | |
| 2016/0065653 A1* | 3/2016 | Chen | H04L 67/10 |
| | | | 715/735 |
| 2016/0087933 A1 | 3/2016 | Johnson et al. | |
| 2017/0168885 A1* | 6/2017 | Jain | H04L 43/50 |

OTHER PUBLICATIONS

The Gnumeric Manual, Determining the number of iterations, May 21, 2015, The Gnumeric Manual, version 1.10, http://www.hep.by/gnu/gnumeric/sect-advanced-analysis-simulation-iterations.shtml (Year: 2015).*

PCT International Search Report, PCT Application No. PCT/US2017/043624, dated Nov. 7, 2017, 3 pages.

* cited by examiner

900

COMPLIANCE CHECKER FOR SERVICE AGREEMENT

CROSS-REFERENCE TO RELATED APPLICATION

The present application claims the benefit of the filing date of U.S. Provisional Patent Application No. 62/379,322, filed Aug. 25, 2016, which is incorporated herein by reference.

TECHNICAL FIELD

The present techniques relate generally to Internet of Things (IoT) devices. More specifically, the present techniques relate to IoT solution characterization for determining compliance with a service agreement for an IoT system.

BACKGROUND

One view of the internet is the connection of clients, such as personal computers, tablets, smart phones, servers, digital photo-frames, and many other types of devices to publicly-accessible data-centers hosted in server farms. However, this picture represents a small portion of the overall usage of the globally-connected network. A very large number of connected resources currently exist, but are not publicly accessible. Examples include corporate networks, private organizational control and monitoring networks spanning the globe, and peer to peer relays designed for anonymity.

The Internet of Things (IoT) may bring Internet connectivity to as many as 50 billion devices by 2020. For organizations, IoT devices may provide opportunities for monitoring, tracking, or controlling other devices and items, including further IoT devices, other home and industrial devices, items in manufacturing and food production chains, and the like. Further, the emergence of IoT networks has served as a catalyst for profound change in the evolution of the internet. In the future, the internet is likely to evolve from a primarily human-oriented utility to an infrastructure where humans may eventually be minority actors in an interconnected world of devices.

In this view, the internet will become a communications system for devices, and networks of devices, to not only communicate with data centers, but with each other. The devices may form functional networks to perform functions, which may dissolve once the function is performed. Challenges exist in enabling reliable, secure, and identifiable devices that can form networks as needed to accomplish tasks.

DESCRIPTION OF THE EMBODIMENTS

Internet of Things (IoT) use case definitions may be characterized by workflows that exercise hardware and software events and interrupts of varying priorities and inter-dependencies. Linear extrapolation of solution characteristics from workflow parameters can lead to inaccuracies that might present a risk to compliance with service agreements such as a Technical Service Level Agreement (TSLA) or other types of service agreements. Embodiments of the present techniques may take some or all guesswork out of modeling the interdependent workflows and platform parameters, and increase the predictive accuracy of service-agreement compliance risk assessment.

A TSLA or similar agreement may be a contract between a technical service provider (either internal or external) and the end user that defines the level of technical service expected from the technical service provider. TSLAs may be output-based in that a purpose can be specifically to define what the customer will receive.

Embodiments disclosed herein relate to the field of Internet of Things data propagation and analysis. Particular reference is made to IoT end points and their associated aggregate devices in the context of end-to-end solution characterization, specifically as it applies to compliance with a service agreement such as a TSLA for the target solution.

Real world deployments may be inherently complex because of the relatively large number of permutations of input workflows. The service-agreement compliance checker (e.g., TSLA compliance checker) described herein evaluates simulated workflows executed on modelled gateway architectures of IoT systems against the benchmarked solutions for compliance. The execution of an exhaustive list of permutations may be made possible because of the implementation of, for example, a back-off algorithm or procedure that systematically identifies and prunes irrelevant iterations, as discussed below.

An IoT solution characterization process that determines service agreement (e.g., TSLA) compliance is discussed herein. Some examples evaluate the simulated workflows on modelled gateways or IoT systems and assess the simulated workflows against quantified service-agreement solution characteristics by means of an integrated lookup table. Evaluation and lookup processes can be extended to function on the edge of sensor modules and sensor hubs, and on data servers within the cloud, and the like.

Figure 1:
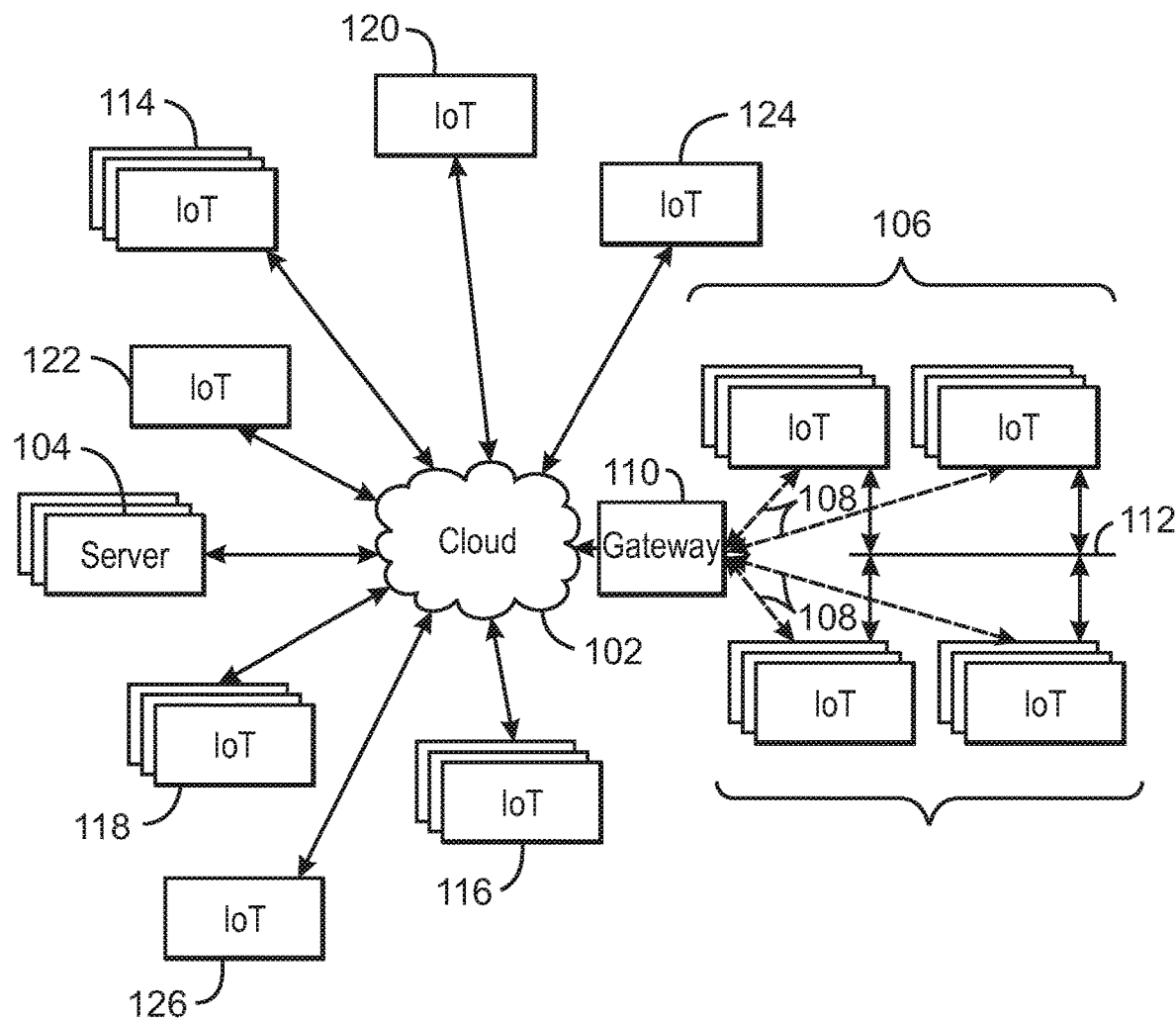
FIG. 1 is a drawing of a cloud computing network, or cloud, in communication with a number of Internet of Things (IoT) devices in accordance with embodiments of the present techniques.

FIG. 1 is a drawing 100 of a cloud computing network, or cloud 102, in communication with a number of Internet of Things (IoT) devices. The cloud 102 may represent the Internet, or may be a local area network (LAN), or a wide area network (WAN), such as a proprietary network for a company. The IoT devices may include any number of different types of devices, grouped in various combinations. For example, a traffic control group 106 may include IoT devices along streets in a city. These IoT devices may include stoplights, traffic flow monitors, cameras, weather sensors, and the like. The traffic control group 106, or other subgroups, may be in communication with the cloud 102 through wireless links 108, such as low-power wide area (LPWA) links, and the like. Further, a wired or wireless sub-network 112 may allow the IoT devices to communicate with each other, such as through a local area network, wireless local area network, and the like. The IoT devices may use another device, such as a gateway 110 to communicate with the cloud 102. In some examples, the sub-network 112 may couple one or more of the IoT devices to the gateway 110 using a wired network.

Moreover, the IoT devices may also use one or more servers (not shown) operationally disposed along the gateway 110, or between the group 106 and the gateway 110, to facilitate communication of the group 106 with the cloud 102 or with the gateway 110. For example, the one or more servers may operate as an intermediate network node to support a local edge cloud or fog implementation among a local area network. The gateway 110 and the one or more servers may be real, virtual, or simulated.

The network topology may include various types of IoT networks, such as a mesh network via Bluetooth® low energy (BLE) links. Other types of IoT networks may include a wireless local area network (WLAN) to communicate with IoT devices through IEEE 802.11 (Wi-Fi®) links, a cellular network to communicate with IoT devices through an LTE/LTE-A (4G) or 5G cellular network, and a LPWA network. A LPWA network may be compatible with the long range wide area network (LoRaWAN™) specification promulgated by the LoRa alliance. The network topology or IoT network(s) may include IPv6 over Low Power Wide-Area Networks (LPWANs) compatible with a specification promulgated by the Internet Engineering Task Force (IETF). Further, the respective IoT networks may communicate with an outside network provider (e.g., a tier 2 or tier 3 provider) via a variety of communications links, such as an LTE cellular link, an LPWA link, or a link based on the IEEE 802.15.4 standard, such as Zigbee®, and so on. The respective IoT networks may also operate by network and internet application protocols such as Constrained Application Protocol (CoAP). The respective IoT networks may also be integrated with coordinator devices that provide a chain of links that forms cluster tree of linked devices and networks.

Although wireless networks and wired networks are described, such as LPWA links, optical links, and the like, it may be noted that any type of network may be used to couple the devices to each other or to a gateway 110. A network or assembled group of devices may have both wired and wireless connections, and may use both simultaneously between nodes, peers, and gateway devices. Further the network or assembled group of devices may use wired networks, wireless networks, or both, to communicate with the cloud, and any higher performance computing devices that may be participating to deliver services or support to what is disclosed herein. Thus, any link 108 or network 112 may utilize a wired connection or a wireless connection. Further, IoT devices may be in direct communications with other devices in the cloud 102 without the use of a gateway 110. The backbone links 108 may include various wired or wireless technologies, including optical networks and, again, may be part of a LAN, a WAN, or the Internet. Additionally, such communication links facilitate optical signal paths among both IoT devices with the cloud 102 and the gateway(s) 110, including the use of MUXing/deMUXing components that facilitate interconnection of the various devices.

IoT devices may include temperature sensors, remote weather stations 114, local information terminals 116, alarm systems 118, automated teller machines 120, alarm panels 122, or moving vehicles, such as emergency vehicles 124 or drones 126, among many others. Each of these IoT devices may be in communication with other IoT devices, with servers 104, or both. The IoT devices or servers 104 may be real, virtual, or simulated.

As can be seen from FIG. 1, a large number of IoT devices may be communicating through the cloud 102. This may allow different IoT devices to request or provide information to other devices autonomously. For example, the traffic control group 106 may request a current weather forecast from a group of remote weather stations 114, which may provide the forecast without human intervention. Further, an emergency vehicle 124 may be alerted by an automated teller machine 120 that a burglary is in progress. As the emergency vehicle 124 proceeds towards the automated teller machine 120, it may access the traffic control group 106 to request clearance to the location, for example, by lights turning red to block cross traffic at an intersection in sufficient time for the emergency vehicle 124 to have unimpeded access to the intersection.

Compliance with the terms of a service agreement or TSLA may be important in the traffic example given above. For example, transit time may be a TSLA term. As used herein, transit time is the time needed for information to travel from one IoT device to another. In the traffic example given above, the time it takes for information to travel from the automated teller machine to the emergency vehicle should comply with the transit time specified in the TSLA, so that the emergency vehicle reaches the automated teller while the burglary is still in process.

Furthermore, as indicated, components shown in FIG. 1, such as the gateway and various sensors or servers, may be real, virtual, or simulated. Indeed, the representations depicted in FIG. 1 may be real or simulated with respect to their depiction and evaluation, including in any hybrid operation of the live IoT components with simulated or emulated components. Moreover, clusters of IoT devices, such as the remote weather stations 114 or the traffic control group 106, may be equipped to communicate with other IoT devices as well as with the cloud 102. This may allow the IoT devices to form an ad-hoc network or virtual network between the devices, allowing them to function as a single device, which may be termed a fog device. This is discussed further with respect to FIG. 2.

Figure 2:
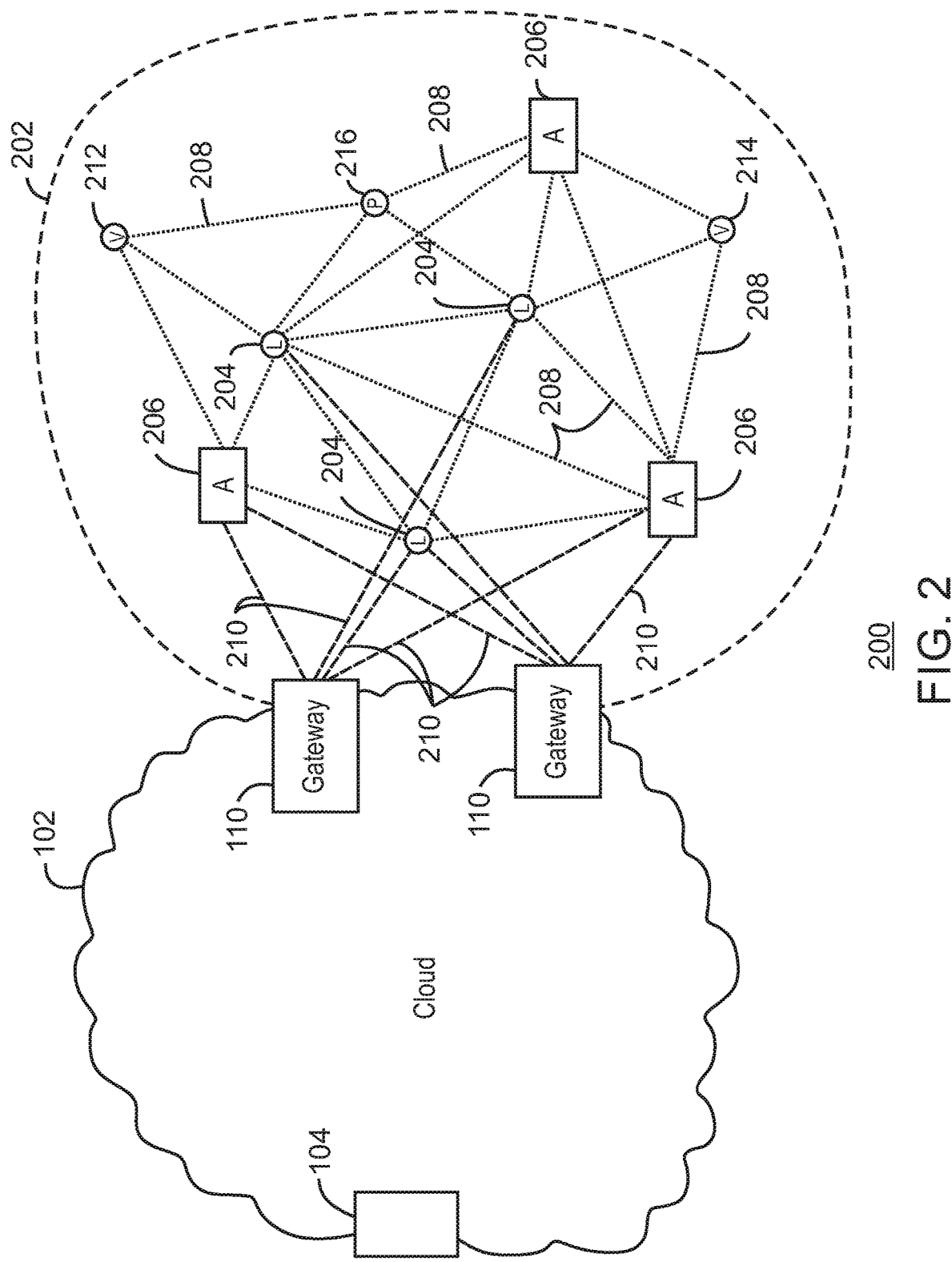
FIG. 2 is a drawing of a cloud computing network, or cloud, in communication with a mesh network of IoT devices, which may be termed a fog device, operating at the edge of the cloud in accordance with embodiments of the present techniques.

FIG. 2 is a drawing 200 of a cloud computing network, or cloud 102, in communication with a mesh network of IoT devices, which may be termed a fog device 202, operating at the edge of the cloud 102. Like numbered items are as described with respect to FIG. 1. As used herein, a fog device 202 is a cluster of devices that may be grouped to perform a specific function, such as traffic control, weather monitoring, plant control, home monitoring, and the like.

Although the fog device 202 is shown as a mesh network in this example, using gateways 110 to communicate with devices in the cloud 102, the devices do not have to be part of a mesh network, or even proximate to each other to form a fog device. Thus, the devices do not have to be in direct radio or network communications with each other, or proximate to each other, but may form an ad hoc group based on function. The formation of the fog device 202 may be as simple as sharing naming, type, and identification information, for example, group identity credentials, between the different devices forming the fog device. This may allow any device to act as a representative of the fog device 202, with providing identity specific to the device. As an example, although the fog device 202 is this example is shown as being made up of devices in a single location, fog devices can include devices in multiple locations, formed to provide specific services. For example, the fog device 202 may include remote weather stations located in the cloud 102. Further, a server 104 located in a data center may be included in the fog device 102 for data analysis, and other services.

In this example, the fog device 202 is a group of IoT devices at an intersection. The fog device 202 may be established in accordance with specifications released by the OpenFog Consortium (OFC), among others. These specifications allow the formation of a hierarchy of computing elements between the gateways 110 coupling the fog device 202 to the cloud 102 and endpoint devices, such as traffic lights 204 and data aggregators 206 in this example. The fog device 202 can leverage the combined processing and network resources that the collective of IoT devices provides. Moreover, the server 104, IoT devices generally and endpoint devices may be real, virtual, or simulated.

Traffic flow through the intersection may be controlled by a plurality of traffic lights (e.g., three traffic lights 204). Analysis of the traffic flow and control schemes may be implemented by aggregators 206 that are in communication with the traffic lights 204 and each other through a mesh network. Data may be uploaded to the cloud 102, and commands received from the cloud 102, through gateways 110 that are in communication with the traffic lights 204 and the aggregators 206 through the mesh network.

Any number of communications links may be used in the fog device 202. Shorter-range links 208, for example, compatible with IEEE 802.15.4 may provide local communications between IoT devices that are proximate to the intersection. Longer-range links 210, for example, compatible with LPWA standards, may provide communications between the IoT devices and the gateways 110. To simplify the diagram, not every communications link 208 or 210 is labeled with a reference number. Further, not every device that participates in the fog device 202 needs to be located proximate to the other devices or in direct radio communications. For example, the fog device 202 may incorporate a weather station located on a different network.

One or more of the communications links 208 and 210 may be replaced with a wired connection between two devices. The network forming the fog device 202 does not have to be a mesh network, but may be a standard network in which each device is coupled to other devices through a wired or wireless connection to the gateways 110.

The fog device 202 may be considered to be an interconnected network wherein a number of IoT devices are in communications with each other, for example, by the communication links 208 and 210, through the cloud 102 via a network communications link, or through a gateway 110. For devices proximate to one another, the network may be established using the open interconnect consortium (OIC) standard specification 1.0 released by the Open Connectivity Foundation™ (OCF) on Dec. 23, 2015. This standard allows devices to discover each other and establish communications for interconnects. Other interconnection protocols may also be used, including, for example, the optimized link state routing (OLSR) Protocol, or the better approach to mobile ad-hoc networking (B.A.T.M.A.N.), among many others.

In some aspects, communications from any IoT device may be passed along the most convenient path between any of the IoT devices to reach the gateways 110, for example, the path having the fewest number of intermediate hops, or the highest bandwidth, among others. In these networks, the number of interconnections provides substantial redundancy, allowing communications to be maintained, even with the loss of a number of IoT devices.

In some aspects, the fog device 202 can include temporary IoT devices. In other words, not all of the IoT devices may be permanent members of the fog device 202. In the example in the drawing 200, three transient IoT devices have joined the fog device 202, a first vehicle 212, a second vehicle 214, and a pedestrian 216. In these cases, the IoT device may be built into the vehicles 212 and 214, or may be an App on a cell phone carried by the pedestrian 216.

The fog device 202 of the devices may be presented to clients in the cloud 102, such as the server 104, as a single device located at the edge of the cloud 102. Again, the server 104 or various IoT devices may be real, virtual, or simulated. In this example, the control communications to specific resources in the fog device 202 may occur without identifying any specific IoT device within the fog device 202. Accordingly, if an IoT device fails, other IoT devices may be able to discover and control a resource. For example, the traffic lights 204 may be wired so as to allow any one of the traffic lights 204 to control lights for the other traffic lights 204.

In some examples, the IoT devices may be configured using an imperative programming style, e.g., with each IoT device having a specific function and communication partners. However, the IoT devices forming the fog device 202 may be configured in a declarative programming style, allowing the IoT devices to reconfigure their operations and communications, such as to determine needed resources in response to conditions, queries, and device failures. This may be performed as transient IoT devices, such as the pedestrian 216, join the fog device 202. As the pedestrian 216 is likely to travel more slowly than the vehicles 212 and 214, the fog device 202 may reconfigure itself to ensure that the pedestrian 216 has sufficient time to make it through the intersection. This may be performed by forming a temporary group of the vehicles 212 and 214 and the pedestrian 216 to control the traffic lights 204. If one or both of the vehicles 212 or 214 are autonomous, the temporary group may instruct the vehicles to slow down prior to the traffic lights 204.

As the transient devices 212, 214, and 216, leave the vicinity of the intersection the fog device 202, it may reconfigure itself to eliminate those IoT devices from the network. As other transient IoT devices approach the intersection, the fog device 202 may reconfigure itself to include those devices.

The fog device 202 may include the traffic lights 204 for a number of intersections, such as along a street, along with all of the transient IoT devices along the street. The fog device 202 may then divide itself into functional units, such as the traffic lights 204 and other IoT devices proximate to a single intersection. This type of combination may enable the formation of larger IoT constructs in the fog device 202. For example, if an emergency vehicle joins the fog device 202, an emergency construct, or virtual device, may be created that includes all of the traffic lights 204 for the street, allowing control of the traffic flow patterns for the entire street. The emergency construct may instruct the traffic lights 204 along the street to stay red for opposing traffic and green for the emergency vehicle, expediting the passage of the emergency vehicle. Lastly, while this discussion may focus on a traffic example, many other applications are relevant and applicable.

Continuing with the traffic example, service-agreement compliance may be important for expediting the passage of an emergency vehicle. For example, the traffic lights should go from green to red for opposing traffic and from red to green for the emergency vehicle, within a particular period of time. Otherwise, the passage of the emergency vehicle may not be expedited.

Certain embodiments provide for an IoT system to perform simulations of the IoT system itself. For instance, simulation code may be stored and executed on the fog device 202, the aggregation device 302 of FIG. 3, or on other devices in an IoT system, such as the data aggregators 206 of the fog device 202. The simulation provides for considering various simulated conditions of the IoT system. In evaluation or operation, the IoT devices of FIG. 2 may be real, virtual, or simulated.

Simulations may include different workloads on the existing IoT architecture giving resulting solution characteristics. In some examples, the simulation system disposed in the IoT system may iterate through simulated incremental values of workload values, architecture or gateway values, and observed solution characteristics values. In particular examples, the simulations may provide for reconfiguration of a fog device 202, for example, by modelling a change in which IoT devices are used to provide particular functions. In other examples, the simulations may provide for consideration of service agreement (e.g., TSLA) requirements and impact on the IoT system, and if service-agreement requirements including new provisions in the service agreement can be satisfied.

Moreover, an IoT simulation system may be installed and executed on an existing or new fog device 202, existing or new aggregation device 302, on other new devices, or on other devices in an existing IoT system. Also, the IoT simulation system or simulation code may be stored and executed on a server, cloud server, remote computer, desktop computer, and so on. The installation of the IoT simulation system may allow for the creation of IoT devices that include both virtual and real IoT devices. Indeed, such may be in reference to a hybrid setup of real and simulated devices. The virtual IoT device may allow for testing different configurations of IoT devices, for example, before adding additional IoT devices to a fog device 202 or reconfiguring communications in a fog device 202. The test results may determine functionality, stability, and the like, as the configuration changes. Further, the IoT system may be monitored and observed in real time for service-agreement compliance. Indeed, the simulations for evaluating compliance and architecture may run and operate in an environment where both live IoT systems and the simulation/emulation are running together to consider, for example, an expansion of an IoT system by testing the proposed architecture. Thus, embodiments may include a hybrid of live and simulated/emulated systems. This hybrid set-up may accommodate testing of, for example, system capacity and fault recovery scenarios.

Figure 3:
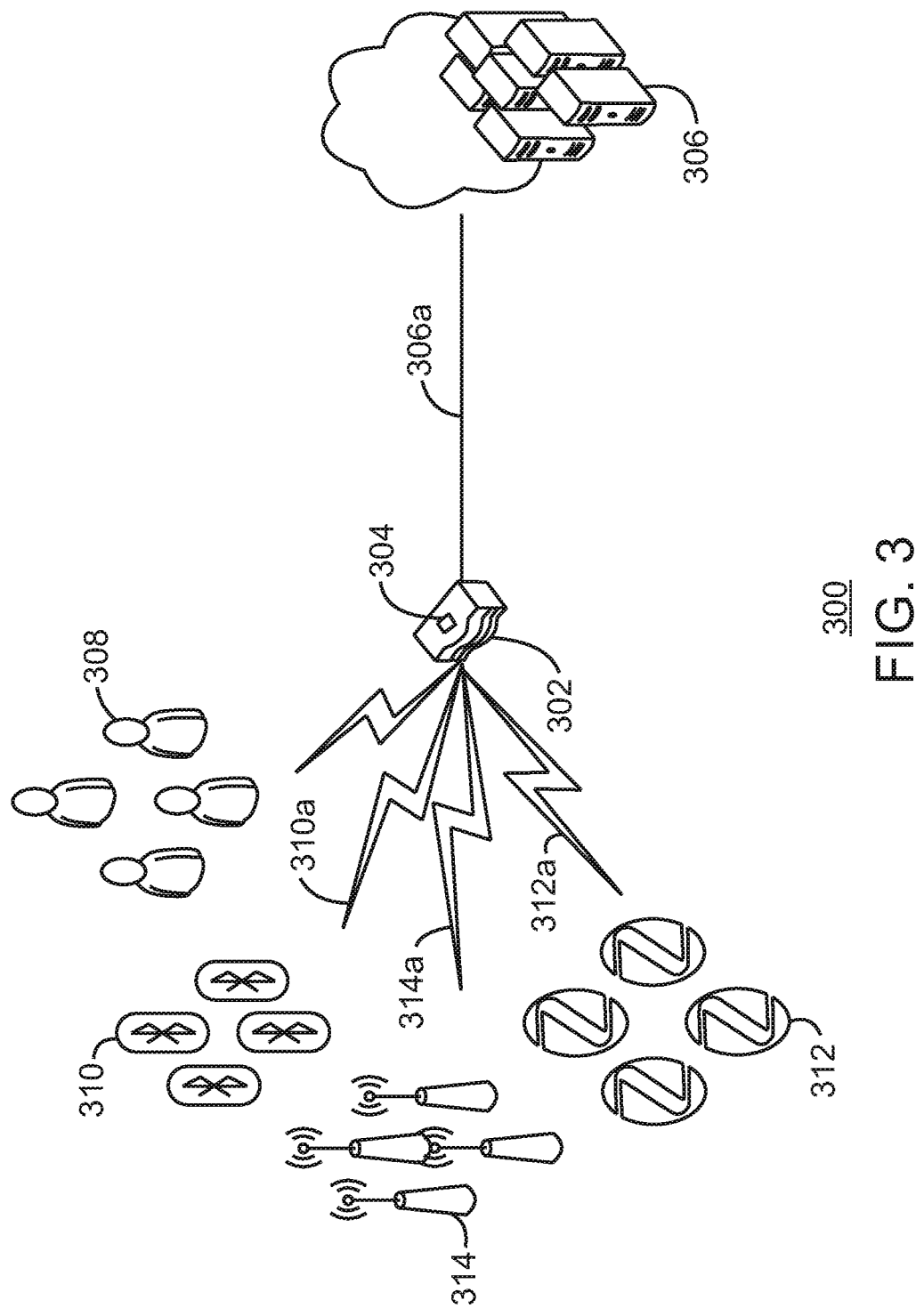
FIG. 3 is an illustration of an end-to-end IoT implementation in accordance with embodiments of the present techniques.

FIG. 3 is an illustration of an IoT system 300 such as an end-to-end IoT implementation system. An aggregation device 302 (e.g., gateway, edge device, etc.) may store code 304 (e.g., instructions, logic, etc.) executable by a processor of the aggregation device 302 to implement techniques discussed herein. In certain embodiments, the aggregation device 302 may be the device 700 of FIG. 7. In addition to or in lieu of the aggregation device 302, the code 304 may be stored and executed on other devices (e.g., FIGS. 7 and 9) such as the servers 306, a computer of a design engineer or service technician, sensor devices, IoT devices generally, and the like. The gateways or aggregation devices 302, servers 306, and sensors discussed below may be real, virtual, or simulated.

Figure 4:
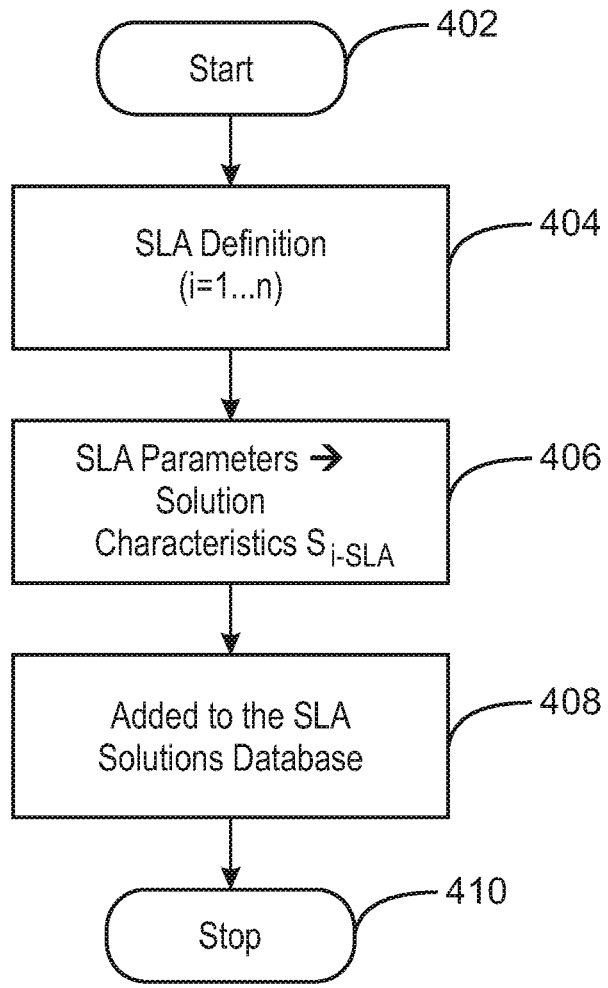
FIG. 4 is a flowchart of a method for building a derived solution characteristics database in accordance with embodiments of the present techniques.
Figure 5:
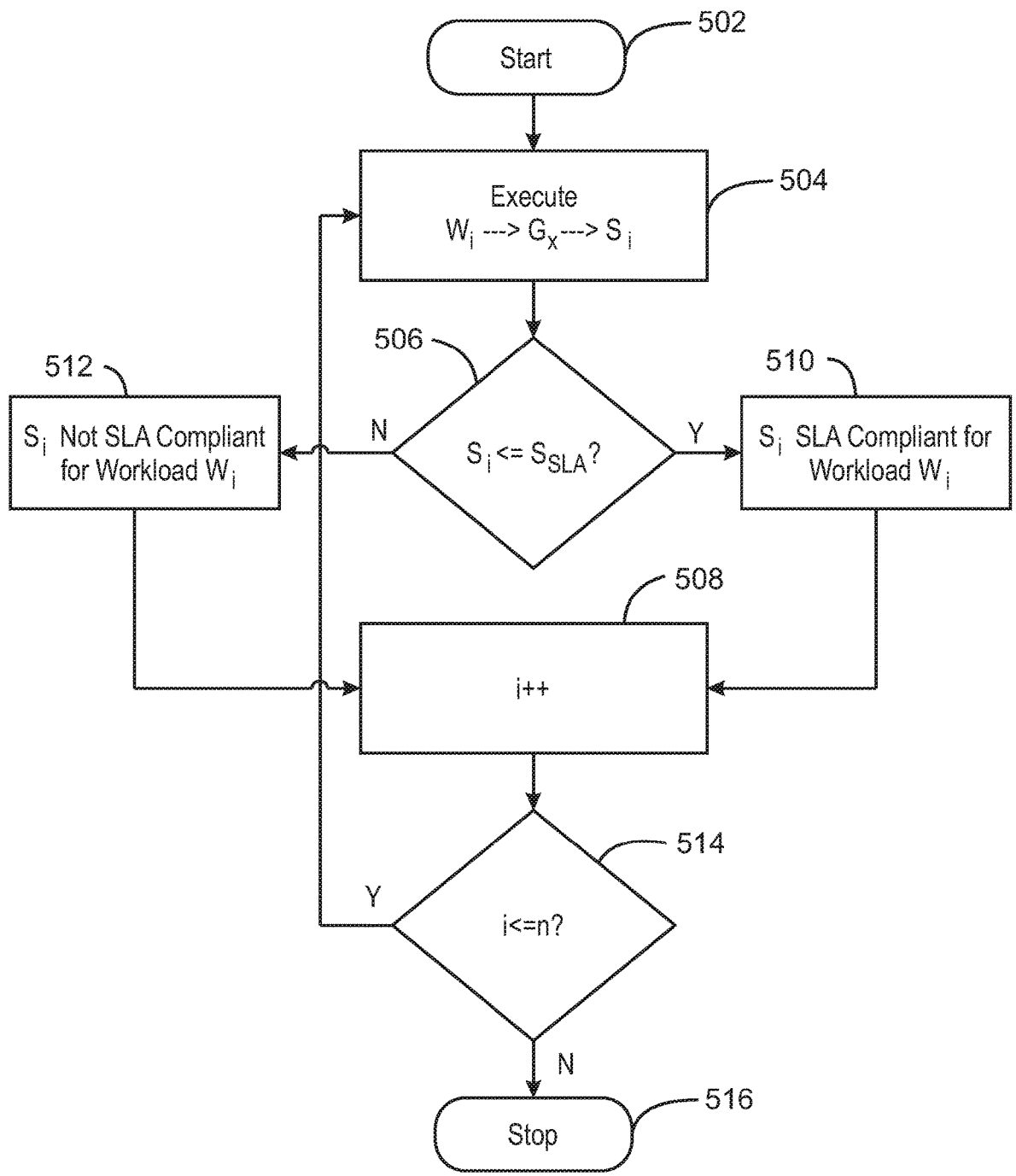
FIG. 5 is a flowchart of a method for evaluating workloads that violate service agreement terms in accordance with embodiments of the present techniques.
Figure 6:
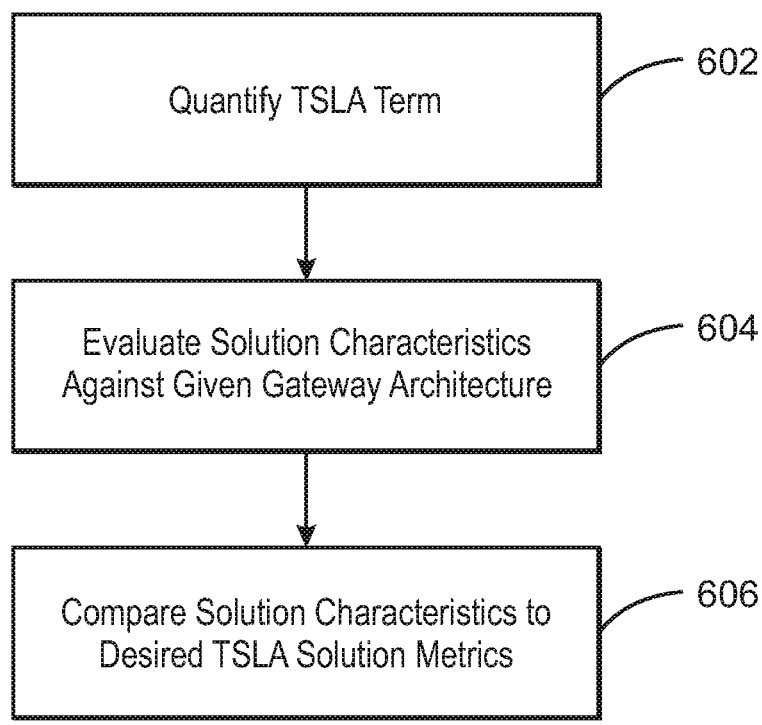
FIG. 6 is a flowchart of a method for checking compliance with a service agreement in accordance with embodiments of the present techniques.

In some embodiments, the database discussed below with respect to FIG. 4 is developed or built on the aggregation device 302 or other device in the IoT system 300. In another embodiment, the database discussed below with respect to FIG. 4 is developed or built on a computing device remote from the IoT implementation system 300, and the database and compliance techniques (e.g., FIGS. 5 and 6) are applied and executed via the aggregation device 302. In other embodiments, the techniques with respect to FIGS. 4-6 are executed via a remote computing device.

In operation, workflow parameters are received by or input to the aggregation device 302 or remote computing device, such as via the servers 306, administrators or end-users 308, sensors 310, 312, 314, and other entities. Examples of input workflow parameters include publish frequency, burst size, data size, total number of sensors, and so on. In the illustrated embodiment, the sensors 310, 312, 314 communicate with the aggregation device 302 by Bluetooth® 310*a*, ZigBee® 312*a*, wireless 314*a* (e.g., Wi-Fi Direct™ or via an access point router), and other wireless communication protocols.

The aggregation device 302 or other computing device quantifies a service-agreement requirement into a simulated solution characteristic. Service-agreement requirements that are quantified may include transactional latency, time to transit, free memory, CPU utilization, and so forth. The simulated solution characteristics for the service-agreement requirements may be generated at or provided to the aggregation device 302, a server, or a remote computing device. Actual solution (observed) characteristics are output. Examples of output solution characteristics may include sensor registration delay, CPU utilization, memory degradation impact, latency limits, and the like. Embodiments for combining workflow parameters and simulated solution characteristics to produce output solution characteristics are discussed in more detail below.

The edge infrastructure in FIG. 3 may refer to the various systems within the defined physical premise, e.g., most or every computing device but the cloud servers 306. The edge infrastructure generally includes the sensor network 310, 312, 314 and the gateways 302, and sometimes includes servers that reside within the edge and are used for back-up, visualization, and management. The edge infrastructure may include at least three components that provide for compliance checking, a control user interface (UI), an automation framework, and an IoT database. These three components are sensors 310, 312, 314, aggregation devices 302, e.g. gateways and hubs, and on-premise servers. Again, the gateways, sensors, servers, and so on, may be real, virtual, or simulated.

The control UI facilitates access to configuration parameters such as the number of sensors, sensor publish frequencies, packet sizes, burstiness of the traffic profiles, quality of service (QoS) values of Message Queuing Telemetry Transport (MQTT) based transmissions, and the like. The configuration parameters are of the edge infrastructure or IoT system 300. The configuration parameters may be stored and accessible in the aggregation device 302 or other computing device, including in a database. The control UI may have the ability to dynamically modify runtime parameters, a characteristic that gives the edge infrastructure the ability to represent real world scenarios. The control UI may initiate monitoring daemons in devices controlled via the UI, such as in sensor hubs, sensors, gateways, cloud servers, etc. The monitoring daemons may facilitate measuring or determining actual solution (observed) characteristics. The monitoring daemons may reside on the gateway 302 or other computing device, and may evaluate certain characteristics that are associated with or unique to the operating conditions of the deployment. The characteristics that may be evaluated include transactional latencies, end-to-end latencies, buffer/queue utilization, memory, CPU consumption, etc.

As to the automation framework, the edge infrastructure may provide application program interfaces (APIs) for defined trigger scripts to interact. For example, the APIs may be stored and executed on the aggregation device or other computing device. Trigger scripts may be a set of executables that can be invoked in response to a set of trigger conditions. For instance, a gateway may send a trigger notification to a peer gateway to activate a series of filters in response to an observed security threat.

The IoT database may be an important component of the edge infrastructure or IoT system. Workflow configuration parameters, results logging, binary searches and pruning based on results from prior runs may be made possible, for instance, by a structured query language (SQL) enabled integrated database or similarly-enabled database. In some examples, most or all interactions with the database may be via the control UI. This arrangement may facilitate security and integrity of the stored data. Workflow configuration information, observed system performance, and the resulting solution characteristics may be mapped in each tuple in the edge infrastructure's database. This correlation enables the building of functions and the extrapolation of solution characteristics and system performance for a range of incrementing workload parameters thus giving the edge architecture the ability to run thousands of permutations to identify beneficial or optimal hardware and/or application what-if scenarios. In certain cases, service-agreement requirements are exercised when the target platform is still under development. The proposed IoT edge infrastructure as illustrated in FIG. 3 consists of a gateway model. Various permutations of gateway architectures enable the user to execute the various workflows through each of these permutations. The number of permutations could result in millions of runs with just a few permutations. In certain embodiments, the service-agreement solutions lookup table helps contain the number of executions by only allowing those permutations that are compliant and terminating the incremental series. Moreover, in general, an IoT solution implementation may be a complex interconnect of edge sensor modules of constantly varying publish characteristics, an aggregation module where data from the sensor modules is aggregated for north bound propagation to central cloud services, and a higher-level aggregation point wherein intelligent decision making, analytics engineering and actuation logic takes place.

All of the devices depicted in the IoT system 300 of FIG. 3 can represent physical devices that are existing and real. However, any of the devices depicted in the IoT system 300 of FIG. 3 could be virtual or simulated. Indeed, the architectural elements disclosed herein such as IoT objects, network entities, servers, gateways, or other nodes can be real, virtual, or simulated. There may be an interchangeability of real, virtual, and simulated elements with respect to the depictions and representations of IoT system devices in the present specification and drawings. Moreover, the simulations for evaluating compliance and architecture may run and operate in an environment where both live IoT systems and the simulation/emulation are running together to evaluate, for example, an expansion of an IoT system by testing the proposed architecture. Thus, embodiments may include a hybrid of live and simulated/emulated systems. This hybrid set-up may accommodate testing of, for instance, system capacity and fault recovery scenarios. Moreover, the proposed expansion of an architecture may involve already-installed or existing devices outside of the IoT system which the IoT system will incorporate or tie into, or can involve new IoT devices to be installed, and so on.

The technique to determine if a proposed solution is service-agreement compliant may include multiple actions. One action is shown as method 400 in FIG. 4 discussed below and involves quantifying the service-agreement terms in the context of the proposed solution. The "context" may refer to factors under which the term of the service agreement was quantified including, for instance, external factors or the environment under which certain parameters are measured. Indeed, context may be with respect to IoT end points and their associated aggregate devices in the environment of end-to-end characterization, specifically as such applies to compliance with a service agreement for a target solution. Context with respect to a set of external factors may also refer to the hardware architecture such as in regard to system deployment or the target gateway including CPU, memory, and storage specifications, and also whether the gateway architecture is existing or contemplated, and so on. The context may be background under which solution (i.e., observed) characteristics are evaluated against a given gateway architecture of an IoT system. The "proposed solution" may be the contemplated or simulated observed characteristic(s), or potential response of a given architecture for a considered workload, and other features or representations, and so on.

FIG. 4 is a method 400 of building a derived solution characteristics database. At block 402, the method starts. At block 404, customer expectations are represented in terms of service level agreement (SLA) definitions i=1 to n. For example, the SLA definition may be a certain latency. At block 406, the method translates or quantifies the SLA definition into a solution characteristic. For example, if the SLA definition is latency, the quantified solution characteristic may be percent central processing unit (CPU) usage, and so forth. At block 408, the quantified solution characteristics for the respective SLA definitions may be placed in a database. The database may provide a lookup table for the present techniques in determining whether the architectures satisfy or violate an SLA definition. At block 410, the method ends.

In one example, a service-agreement requirement could be the ability of the system administrator to access the login console and execute system commands in the event of a denial of service (DoS) attack. In that example, service-agreement solution requirements could be 5% CPU and 0.2% memory consumed by console login and system command execution, and the system events and workload characteristics to collectively contribute no more than 20% CPU and 95% memory utilization during workflow execution runs. The workflows in FIG. 4 are simulated workflows and are further described with respect to FIG. 5.

The service-agreement quantification may be an action in the service-agreement compliance process. A subsequent action may be to evaluate workflows, evaluate the solution, or observed characteristics, against the given gateway architecture, and compare these solution characteristics with the desired service-agreement solution metrics by means of a lookup process, for instance. Each workflow permutation may be exercised in this manner using an iteration generator until most or all target input workflows have been exhausted.

The iteration generator may be an automation utility within the control UI that facilitates the user's choice of configuration values for a plurality of input parameters, such as those shown below in Table 1.

TABLE 1

Example Values of Exemplary Workload Parameters

| Input Workload Parameter | Value |
| --- | --- |
| File Size (MB) | 100, 200, 300, 400, 500 |
| USB Access Time (ms) | 1 |
| USB Interface Throughput (MB/s) | 12, 480, 640 |
| Video Location | Local Disk, USB |
| Wifi Throughput (MB/s) | 100, 1000 |
| CPU Frequency (MGHz) | 1460, 1800 |
| CPU Cores | 0, 1, 2, 4 |
| Sensor count | 1, 30, 50 |
| FFMPEG process | True, false |
| Low Priority Process Running Time (ms) | 100, 300 |
| High Priority Process Running Time (ms) | 30, 60 |
| Enable Mosquito Process | True, False |
| RAM Size (GB) | 4, 8, 16, 32 |
| Sensor Data Size (bytes) | 16, 32, 64, 128 |
| Enable Low Priority Process | True, False |
| Enable High Priority Process | True, False |
| Network Interface Throughput (MB/s) | 100, 1000 |
| Enable Sensors | True, False |
| Scheduler Policy | PRIORITY_NON_PREEMTIVE, PRIORITY_PREEMTIVE |

The utility builds most or all possible permutations of the stated input values and triggers run lines for a series of automation runs that are generally executed sequentially. This may give the user the capability to identify limiting conditions as the input parameters and facilitates the system's determination of a beneficial or optimal set of workflow and architectural options identified within the stated boundary conditions.

FIG. 5 is a flowchart of a method 500 for evaluating workloads that may satisfy or violate service-agreement terms. The method starts at block 502. At block 504, the method assigns workloads $W_i$ and the associated solution or observed characteristics $S_i$ to a given architecture $G_x$ of an edge or IoT system. At block 506, a decision is made as to whether the characteristics $S_i$ are less than or equal to the relevant service-agreement (e.g., TSLA) terms $S_{SLA}$. The comparison may involve use of a lookup table of a database as developed with respect to the method of FIG. 4, for example. If the comparison in block 506 indicates that $S_i$ satisfies the $S_{SLA}$, the $S_i$ is service-agreement (e.g., service level agreement or SLA) compliant for the workload $W_i$, as indicated in block 510. If the comparison in block 506 indicates that $S_i$ does not satisfy the $S_{SLA}$, the $S_i$ is not SLA compliant for the workload $W_i$, as indicated in block 512. At block 508, i is incremented. At block 514, the method repeats if the number i of workload characteristics $W_i$ and solution characteristics $S_i$ is less than a desired number n. When the number i reaches n, the iteration or method may be complete, as indicated by 516.

FIG. 6 is a flow chart of a method 600 for checking compliance with a service agreement such as a TSLA. At block 602, a term of a service agreement is quantified in the context of the proposed solution. For example, a TSLA item may refer to sensor latency registration times quantified via a reference in seconds within a stated context, which refers to the external factors under which the latencies were measured. Moreover, the context of the proposed solution may refer to factors under which the term of the service agreement was quantified. Furthermore, while "TSLA" is depicted in block 602, a different type of service agreement is applicable to method 600. At block 604, solution (i.e., observed) characteristics are evaluated against a given gateway architecture of an IoT system. For instance, the defined set of external factors may also refer to the hardware architecture of the system used in the deployment or to the CPU, memory, and storage specifications of a target gateway. Furthermore, the gateway architecture may be an existing architecture or a proposed/contemplated architecture. At block 606, the solution characteristics are compared to the desired service-agreement solution metrics. In other words, the solution characteristics predicted by the model may now be compared against a set of requirements defined by the TSLA for compliance. The method of FIG. 6 may include accessing and modifying a configuration parameter via a control user interface (UI). The method may also include controlling sensor hubs, sensors, gateways, and cloud servers via the control UI. The method may further include initiating monitoring daemons in the aforementioned devices controlled by the control UI. The control UI may also access a database. Data may be mapped in a tuple in the database.

In the method of FIG. 6, configuration values for a plurality of input parameters may be chosen utilizing an iteration generator. The method 600 may also involve interacting defined trigger scripts using application program interfaces. Lastly, it should be noted that Message Queuing Telemetry Transport (MQTT) or similar protocols or technologies may be employed. MQTT is a machine-to-machine (M2M)/IoT connectivity protocol. MQTT was designed as a lightweight publish/subscribe messaging transport and may be useful for connections with remote locations where a small code footprint is required and/or network bandwidth is at a premium. For example, MQTT has been used in sensors communicating to a broker via satellite link, over occasional dial-up connections with healthcare providers, and in a range of home automation and small device scenarios. MQTT may also be beneficial for mobile applications because of MQTT's small size, low power usage, minimized data packets, and efficient distribution of information to one or many receivers.

Figure 7:
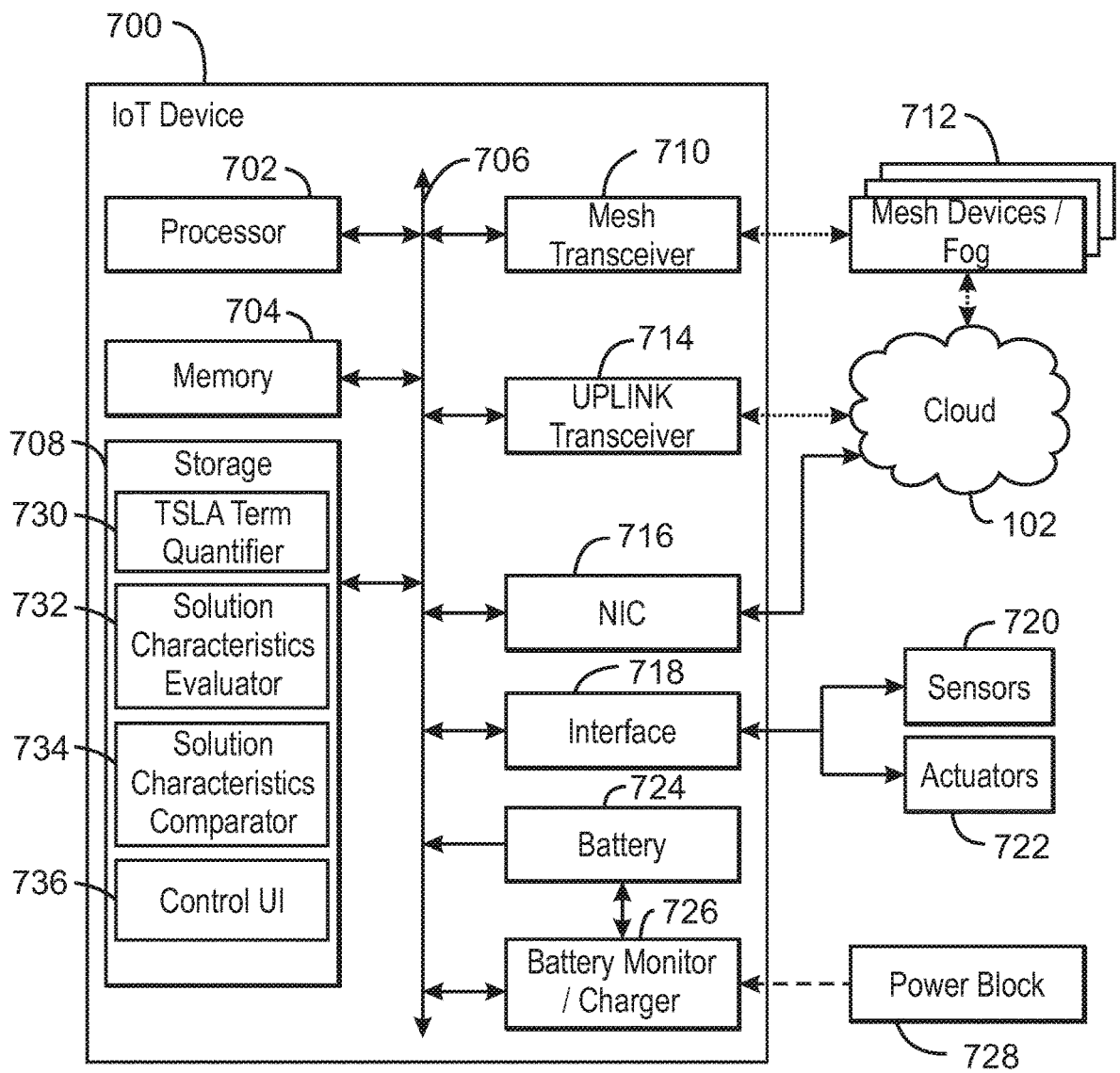
FIG. 7 is a block diagram of an example of components that may be present in an IoT device for offloading data in accordance with embodiments of the present techniques.

FIG. 7 is a block diagram of an example of components that may be present in an IoT device 700 for offloading data. The IoT device 700 may include any combinations of the components shown in the example. The components may be implemented as ICs, portions thereof, discrete electronic devices, or other modules, logic, hardware, software, firmware, or a combination thereof adapted in the IoT device 700, or as components otherwise incorporated within a chassis of a larger system. The block diagram of FIG. 7 is intended to show a high-level view of components of the IoT device 700. However, some of the components shown may be omitted, additional components may be present, and different arrangements of the components shown may occur in other implementations.

The IoT device 700 may include a processor 702, which may be a microprocessor, a multi-core processor, a multi-threaded processor, an ultra-low voltage processor, an embedded processor, or other known processing element. The processor 702 may be a part of a system on a chip (SoC) in which the processor 702 and other components are formed into a single integrated circuit, or a single package, such as the Edison™ or Galileo™ SoC boards from Intel. As an example, the processor 702 may include an Intel® Architecture Core™ based processor, such as a Quark™, an Atom™, an i3, an i5, an i7, or an MCU-class processor, or another such processor available from Intel® Corporation, Santa Clara, Calif. However, any number of other processors may be used, such as those available from Advanced Micro Devices, Inc. (AMD) of Sunnyvale, Calif., a MIPS-based design from MIPS Technologies, Inc. of Sunnyvale, Calif., an ARM-based design licensed from ARM Holdings, Ltd. or customer thereof, or their licensees or adopters. The processors may include units such as an A5-A9 processor from Apple® Inc., a Snapdragon™ processor from Qualcomm® Technologies, Inc., or an OMAP™ processor from Texas Instruments, Inc.

The processor 702 may communicate with a system memory 704 over a bus 706. Any number of memory devices may be used to provide for a given amount of system memory. As examples, the memory can be random access memory (RAM) in accordance with a Joint Electron Devices Engineering Council (JEDEC) low power double data rate (LPDDR)-based design such as the current LPDDR2 standard according to JEDEC JESD 209-2E (published April 2009), or a next generation LPDDR standard, such as LPDDR3 or LPDDR4 that will offer extensions to LPDDR2 to increase bandwidth. In various implementations, the individual memory devices may be of any number of different package types such as single die package (SDP), dual die package (DDP) or quad die package (Q17P). These devices, in some embodiments, may be directly soldered onto a motherboard to provide a lower profile solution, while in other embodiments the devices are configured as one or more memory modules that in turn couple to the motherboard by a given connector. Any number of other memory implementations may be used, such as other types of memory modules, e.g., dual inline memory modules (DIMMs) of different varieties including but not limited to microDIMMs or MiniDIMMs. For example, a memory may be sized between 2 GB and 16 GB, and may be configured as a DDR3LM package or an LPDDR2 or LPDDR3 memory, which is soldered onto a motherboard via a ball grid array (BGA).

To provide for persistent storage of information such as data, applications, operating systems and so forth, a mass storage 708 may also couple to the processor 702 via the bus 706. To enable a thinner and lighter system design the mass storage 708 may be implemented via a solid state disk drive (SSDD). Other devices that may be used for the mass storage 708 include flash memory cards, such as SD cards, microSD cards, xD picture cards, and the like, and USB flash drives. In low power implementations, the mass storage 708 may be on-die memory or registers associated with the processor 702. However, in some examples, the mass storage 708 may be implemented using a micro hard disk drive (HDD). Further, any number of new technologies may be used for the mass storage 708 in addition to, or instead of, the technologies described, such as resistance change memories, phase change memories, holographic memories, or chemical memories, among others. For example, the IoT device 700 may incorporate the 3D XPOINT memories from Intel® and Micron®.

The components may communicate over the bus 706. The bus 706 may include any number of technologies, including industry standard architecture (ISA), extended ISA (EISA), peripheral component interconnect (PCI), peripheral component interconnect extended (PCIx), PCI express (PCIe), or any number of other technologies. The bus 706 may be a proprietary bus, for example, used in a SoC based system. Other bus systems may be included, such as an I$^2$C interface, an SPI interface, point to point interfaces, and a power bus, among others.

The bus 706 may couple the processor 702 to a mesh transceiver 710, for communications with other mesh devices 712. The mesh transceiver 710 may use any number of frequencies and protocols, such as 2.4 gigahertz (GHz) transmissions under the IEEE 802.15.4 standard, using the Bluetooth® low energy (BLE) standard, as defined by the Bluetooth® Special Interest Group, or the ZigBee® standard, among others. Any number of radios, configured for a particular wireless communication protocol, may be used for the connections to the mesh devices 712. For example, a WLAN unit may be used to implement Wi-Fi™ communications in accordance with the Institute of Electrical and Electronics Engineers (IEEE) 802.11 standard. In addition, wireless wide area communications, e.g., according to a cellular or other wireless wide area protocol, can occur via a WWAN unit.

The mesh transceiver 710 may communicate using multiple standards or radios for communications at different ranges. For example, the IoT device 700 may communicate with close devices, e.g., within about 10 meters, using a local transceiver based on BLE, or another low power radio, to save power. More distant mesh devices 712, e.g., within about 50 meters, may be reached over ZigBee or other intermediate power radios. Both communications techniques may take place over a single radio at different power levels, or may take place over separate transceivers, for example, a local transceiver using BLE and a separate mesh transceiver using ZigBee. The mesh transceiver 710 may be incorporated into an MCU as an address directly accessible by the chip, such as in the Curie® units available from Intel.

An uplink transceiver 714 may be included to communicate with devices in the cloud 102. The uplink transceiver 714 may be LPWA transceiver that follows the IEEE 802.15.4, or IEEE 802.15.4g standards, among others. The IoT device 700 may communicate over a wide area using LoRaWAN™ (Long Range Wide Area Network) developed by Semtech and the LoRa Alliance. The techniques described herein are not limited to these technologies, but may be used with any number of other cloud transceivers that implement long range, low bandwidth communications, such as Sigfox, and other technologies. Further, other communications techniques, such as time-slotted channel hopping, described in IEEE 802.15.4e may be used.

Any number of other radio communications and protocols may be used in addition to the systems mentioned for the mesh transceiver 710 and uplink transceiver 714, as described herein. For example, the radio transceivers 710 and 712 may include an LTE or other cellular transceiver that uses spread spectrum (SPA/SAS) communications for implementing high speed communications, such as for video transfers. Further, any number of other protocols may be used, such as Wi-Fi networks for medium speed communications, such as still pictures, sensor readings, and provision of network communications.

The radio transceivers 710 and 714 may include radios that are compatible with any number of 3GPP (Third Generation Partnership Project) specifications, notably Long Term Evolution (LTE), Long Term Evolution-Advanced (LTE-A), and Long Term Evolution-Advanced Pro (LTE-A Pro). It can be noted that radios compatible with any number of other fixed, mobile, or satellite communication technologies and standards may be selected. These may include, for example, any Cellular Wide Area radio communication technology, which may include e.g. a 5th Generation (5G) communication systems, a Global System for Mobile Communications (GSM) radio communication technology, a General Packet Radio Service (GPRS) radio communication technology, or an Enhanced Data Rates for GSM Evolution (EDGE) radio communication technology. Other Third Generation Partnership Project (3GPP) radio communication technology that may be used includes UMTS (Universal Mobile Telecommunications System), FOMA (Freedom of Multimedia Access), 3GPP LTE (Long Term Evolution), 3GPP LTE Advanced (Long Term Evolution Advanced), 3GPP LTE Advanced Pro (Long Term Evolution Advanced Pro)), CDMA2000 (Code division multiple access 2000), CDPD (Cellular Digital Packet Data), Mobitex, 3G (Third Generation), CSD (Circuit Switched Data), HSCSD (High-Speed Circuit-Switched Data), UMTS (3G) (Universal Mobile Telecommunications System (Third Generation)), W-CDMA (UMTS) (Wideband Code Division Multiple Access (Universal Mobile Telecommunications System)), HSPA (High Speed Packet Access), HSDPA (High-Speed Downlink Packet Access), HSUPA (High-Speed Uplink Packet Access), HSPA+ (High Speed Packet Access Plus), UMTS-TDD (Universal Mobile Telecommunications System—Time-Division Duplex), TD-CDMA (Time Division—Code Division Multiple Access), TD-SCDMA (Time Division—Synchronous Code Division Multiple Access), 3GPP Rel. 8 (Pre-4G) (3rd Generation Partnership Project Release 8 (Pre-4th Generation)), 3GPP Rel. 9 (3rd Generation Partnership Project Release 9), 3GPP Rel. 10 (3rd Generation Partnership Project Release 10), 3GPP Rel. 11 (3rd Generation Partnership Project Release 11), 3GPP Rel. 12 (3rd Generation Partnership Project Release 12), 3GPP Rel. 13 (3rd Generation Partnership Project Release 13), 3GPP Rel. 14 (3rd Generation Partnership Project Release 14), 3GPP LTE Extra, LTE Licensed-Assisted Access (LAA), UTRA (UMTS Terrestrial Radio Access), E-UTRA (Evolved UMTS Terrestrial Radio Access), LTE Advanced (4G) (Long Term Evolution Advanced (4th Generation)), cdmaOne (2G), CDMA2000 (3G) (Code division multiple access 2000 (Third generation)), EV-DO (Evolution-Data Optimized or Evolution-Data Only), AMPS (1G) (Advanced Mobile Phone System (1st Generation)), TACS/ETACS (Total Access Communication System/Extended Total Access Communication System), D-AMPS (2G) (Digital AMPS (2nd Generation)), PTT (Push-to-talk), MTS (Mobile Telephone System), IMTS (Improved Mobile Telephone System), AMTS (Advanced Mobile Telephone System), OLT (Norwegian for Offentlig Landmobil Telefoni, Public Land Mobile Telephony), MTD (Swedish abbreviation for Mobiltelefonisystem D, or Mobile telephony system D), Autotel/PALM (Public Automated Land Mobile), ARP (Finnish for Autoradiopuhelin, "car radio phone"), NMT (Nordic Mobile Telephony), Hicap (High capacity version of NTT (Nippon Telegraph and Telephone)), CDPD (Cellular Digital Packet Data), Mobitex, DataTAC, iDEN (Integrated Digital Enhanced Network), PDC (Personal Digital Cellular), CSD (Circuit Switched Data), PHS (Personal Handyphone System), WiDEN (Wideband Integrated Digital Enhanced Network), iBurst, Unlicensed Mobile Access (UMA, also referred to as 3GPP Generic Access Network, or GAN standard)), Wireless Gigabit Alliance (WiGig) standard, mmWave standards in general (wireless systems operating at 10-90 GHz and above such as WiGig, IEEE 802.11ad, IEEE 802.11ay, and the like. In addition to the standards listed above, any number of satellite uplink technologies may be used for the uplink transceiver 714, including, for example, radios compliant with standards issued by the ITU (International Telecommunication Union), or the ETSI (European Telecommunications Standards Institute), among others. The examples provided herein are thus understood as being applicable to various other communication technologies, both existing and not yet formulated.

A network interface controller (NIC) 716 may be included to provide a wired communication to the cloud 102. The wired communication may provide an Ethernet connection, or may be based on other types of networks, such as Controller Area Network (CAN), Local Interconnect Network (LIN), DeviceNet, ControlNet, Data Highway+, PROFIBUS, or PROFINET, among many others. An additional NIC 716 may be included to allow connection to a second network, for example, a NIC 716 providing communications to the cloud over Ethernet, and a second NIC 716 providing communications to other devices over another type of network.

The bus 706 may couple the processor 702 to an interface 718 that is used to connect external devices. The external devices may include sensors 720, such as accelerometers, level sensors, flow sensors, temperature sensors, pressure sensors, barometric pressure sensors, and the like. The interface 718 may be used to connect the IoT device 700 to actuators 722, such as power switches, valve actuators, an audible sound generator, a visual warning device, and the like.

While not shown, various input/output (I/O) devices may be present within, or connected to, the IoT device 700. For example, a display may be included to show information, such as sensor readings or actuator position. An input device, such as a touch screen or keypad may be included to accept input.

A battery 724 may power the IoT device 700, although in examples in which the IoT device 700 is mounted in a fixed location, it may have a power supply coupled to an electrical grid. The battery 724 may be a lithium ion battery, a metal-air battery, such as a zinc-air battery, an aluminum-air battery, a lithium-air battery, and the like.

A battery monitor/charger 726 may be included in the IoT device 700 to track the state of charge (SoCh) of the battery 724. The battery monitor/charger 726 may be used to monitor other parameters of the battery 724 to provide failure predictions, such as the state of health (SoH) and the state of function (SoF) of the battery 724. The battery monitor/charger 726 may include a battery monitoring integrated circuit, such as an LTC4020 or an LTC2990 from Linear Technologies, an ADT7488A from ON Semiconductor of Phoenix Ariz., or an IC from the UCD90xxx family from Texas Instruments of Dallas, Tex. The battery monitor/charger 726 may communicate the information on the battery 724 to the processor 702 over the bus 706. The battery monitor/charger 726 may also include an analog-to-digital (ADC) convertor that allows the processor 702 to directly monitor the voltage of the battery 724 or the current flow from the battery 724. The battery parameters may be used to determine actions that the IoT device 700 may perform, such as transmission frequency, mesh network operation, sensing frequency, and the like.

A power block 728, or other power supply coupled to a grid, may be coupled with the battery monitor/charger 726 to charge the battery 724. In some examples, the power block 728 may be replaced with a wireless power receiver to obtain the power wirelessly, for example, through a loop antenna in the IoT device 700. A wireless battery charging circuit, such as an LTC4020 chip from Linear Technologies of Milpitas, Calif., among others, may be included in the battery monitor/charger 726. The specific charging circuits chosen depend on the size of the battery 724, and thus, the current required. The charging may be performed using the Airfuel standard promulgated by the Airfuel Alliance, the Qi wireless charging standard promulgated by the Wireless Power Consortium, the Rezence charging standard, promulgated by the Alliance for Wireless Power, among others.

The mass storage 708 may include a number of modules to implement the service-agreement compliance checker functions described herein. Although shown as code blocks in the mass storage 708, it may be understood that any of the modules may be replaced with hardwired circuits, for example, built into an application specific integrated circuit (ASIC). The mass storage 708 may include a service-agreement (e.g., TSLA) term quantifier 730 for quantifying a TSLA term in the context of a proposed solution.

A solution characteristics evaluator 732 may provide evaluation of solution characteristics against a given gateway architecture. A solution characteristics comparator 734 compares the solution characteristics to desired TSLA solution metrics. A control user interface (UI) 736 may provide access and modify a configuration parameter. The control UI 736 may provide for a user to access and modify a configuration parameter. The configuration parameter may be stored in the storage 708 or on another computing device, including in a database. The control UI 736 may include an iteration generator to choose configuration values for input parameters. The control UI 736 may facilitate control of sensor hubs, sensors, a gateway, a cloud server, and so on. The sensor hubs, sensors, and gateway may be real, virtual, or simulated.

Figure 8:
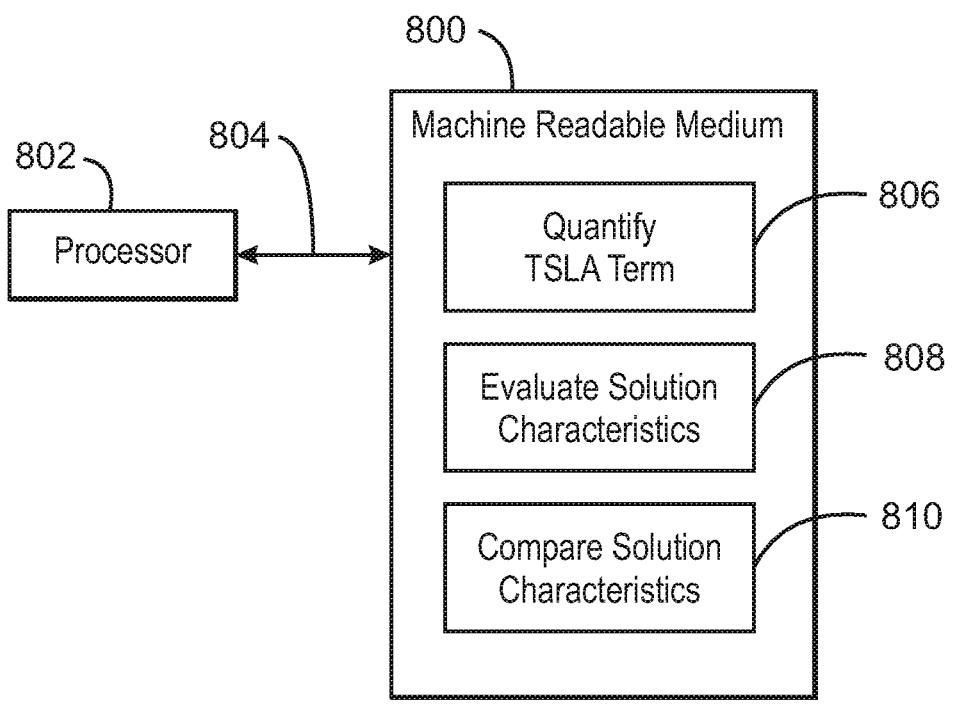
FIG. 8 is a non-transitory machine readable medium in accordance with embodiments of the present techniques.

FIG. 8 is a block diagram of a non-transitory, machine readable medium 800 including code to direct a processor 802 to check for service-agreement compliance. The processor 802 may access the non-transitory, machine readable medium 800 over a bus 804. The processor 802 and bus 804 may be as described with respect to FIG. 7. The non-transitory, machine readable medium 800 may include devices described for the mass storage 708 of FIG. 7 or may include optical disks, thumb drives, or any number of other hardware devices.

The non-transitory, machine readable medium 800 may include code 806 to direct the processor 802 to quantify a service-agreement term in the context of a proposed solution. Code 808 may be included to direct the processor 802 to evaluate solution characteristics against a given gateway architecture. Code 810 may be included to direct the processor 802 to compare solution characteristics to desired service-agreement solution metrics.

Figure 9:
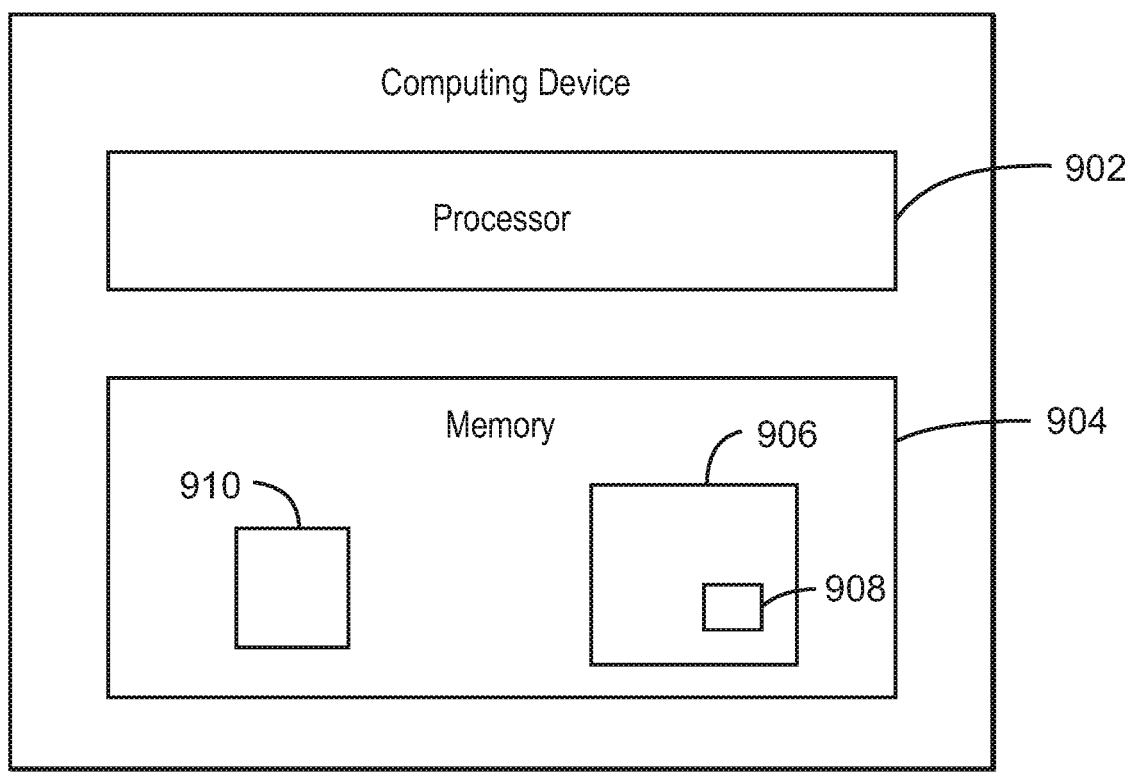
FIG. 9 is a diagram of a computing device for evaluating compliance with a service agreement in accordance with embodiments of the present techniques.

FIG. 9 is a computing device 900 to implement compliance checking of a service agreement such as in the context of an IoT system. The computing device 900 may be an aggregation device, edge device, fog device, smart sensor, server, etc. of an IoT system. The computing device 900 may be a cloud server or a remote computing device, and the like.

The computing device 900 includes a hardware processor 902 such as a microprocessor, a central processing unit (CPU), and so forth. The processor 902 may be multiple processors and each processor 902 may have multiple cores.

The computing device 900 has memory 904, such as non-volatile memory, volatile memory, and other types of memory. The non-volatile memory may be a hard drive, read-only-memory (ROM), etc. The volatile memory may be random access memory (RAM), cache, etc. Further, the computing device 900 may include multiple computing devices 900.

In the illustrated example, the memory 904 stores code 906, e.g., instructions, logic, etc., executable by the one or more processors 902. The code 906 may be executed by the processor 902 to implement the techniques discussed herein. For example, the computing device 900 via the processor 902 and executed code 906 may quantify a term of a service agreement in a context of a proposed solution, evaluate solution characteristics against a given gateway architecture, and compare the solution characteristics to desired solution metrics of the service agreement. As mentioned, the solution characteristics may be a simulated observed characteristic. Moreover, to evaluate and compare may include employing a lookup table stored in a database.

The code 906 may also include a control UI 908 for the computing device 900 to provide a control UI to access and modify a configuration parameter. The control UI 908 may provide for a user to access and modify a configuration parameter. The configuration parameter may be stored in the memory 904, including in the database 910, or may be stored on another computing device. The control UI may include an iteration generator to choose configuration values for a plurality of input parameters. The control UI may facilitate control of sensor hubs, sensors, a gateway, a cloud server, and so on. Moreover, the sensor hubs, sensors, and gateway may be real, virtual, or simulated. The computing device may also include a database(s) 910, as discussed above. In some examples, the database 910 may be accessed via the control UI. Also, the computing device 900 may incorporate an application-specific integrated circuit (ASIC) customized for the techniques described.

Examples are given. Example 1 is an apparatus. The apparatus includes a computing device to check compliance of a service agreement for an IoT system, comprising the computing device to: quantify a term of the service agreement in a context of a proposed solution; evaluate solution characteristics against a given gateway architecture; and compare the solution characteristics to desired solution metrics of the service agreement, wherein the solution characteristics comprise a simulated observed characteristic.

Example 2 includes the apparatus of example 1, including or excluding optional features. In this example, the computing device comprises a control user interface (UI) for a user to access and modify a configuration parameter for the IoT system. Optionally, the configuration parameter comprises at least one of number of sensors, sensor publish frequencies, packet sizes, burstiness of traffic profiles, or quality of service values of Message Queuing Telemetry Transport (MQTT) based transmissions. Optionally, the control UI controls sensor hubs, sensors, a gateway, and a cloud server, and wherein to evaluate and compare comprises to employ a lookup table stored in a database, wherein the control UI comprises an iteration generator, and wherein a user employs the iteration generator to choose configuration values for a plurality of input parameters comprising configuration parameters. Optionally, the apparatus includes a database accessed via the control UI, wherein data mapped in a tuple in the database comprises workflow configuration information, observed system performance, and resulting solution characteristics, and wherein the computing device comprises a processor and memory storing code executable by the processor to quantify the term, evaluate the solution characteristics, and compare the solution characteristics to the desired solution metrics.

Example 3 includes the apparatus of any one of examples 1 to 2, including or excluding optional features. In this example, the context comprises a factor under which the term was quantified.

Example 4 includes the apparatus of any one of examples 1 to 3, including or excluding optional features. In this example, the given gateway architecture is a hybrid comprising live and simulated components.

Example 5 is a method of compliance checking. The method includes quantifying a term of a service agreement for an IoT system in a context of a proposed solution; evaluating solution characteristics against a given gateway architecture; and comparing the solution characteristics to desired solution metrics of the service agreement.

Example 6 includes the method of example 5, including or excluding optional features. In this example, the context comprises a factor under which a parameter is measured.

Example 7 includes the method of any one of examples 5 to 6, including or excluding optional features. In this example, the given gateway architecture comprises a hybrid of real and simulated components.

Example 8 includes the method of any one of examples 5 to 7, including or excluding optional features. In this example, the method includes accessing and modifying a configuration parameter for the IoT system via a control user interface (UI); controlling sensor hubs, sensors, gateways, and cloud servers via the control UI; and initiating monitoring daemons in a device controlled by the control UI. Optionally, the method includes accessing a database via the control UI; and mapping data in a tuple in the database.

Example 9 includes the method of any one of examples 5 to 8, including or excluding optional features. In this example, the method includes choosing, via an iteration generator, configuration values for a plurality of input parameters.

Example 10 includes the method of any one of examples 5 to 9, including or excluding optional features. In this example, the method includes interacting defined trigger scripts via application program interfaces, wherein the service agreement comprises a Technical Service Level Agreement (TSLA).

Example 11 is a tangible, non-transitory, computer-readable medium. The computer-readable medium includes instructions that direct the processor to quantify a term of a service agreement for an IoT system in a context of a proposed solution; evaluate solution characteristics against a given gateway architecture; and compare the solution characteristics to desired service-agreement solution metrics.

Example 12 includes the computer-readable medium of example 11, including or excluding optional features. In this example, the computer-readable medium includes code executable by the processor to direct the processor to provide a control user interface (UI) for a user to access and modify a configuration parameter of the IoT system. Optionally, the computer-readable medium includes code executable by the processor to direct the processor to initiate monitoring daemons in a device controlled by the control UI.

Example 13 includes the computer-readable medium of any one of examples 11 to 12, including or excluding optional features. In this example, the computer-readable medium includes code comprising an iteration generator executable by a processor to direct the processor to choose configuration values for a plurality of input parameters.

Example 14 includes the computer-readable medium of any one of examples 11 to 13, including or excluding optional features. In this example, the context comprises a factor under which the term was quantified.

Example 15 includes the computer-readable medium of any one of examples 11 to 14, including or excluding optional features. In this example, the given gateway architecture is a hybrid comprising live and simulated components.

Example 16 is an IoT system. The system includes an aggregation device; at least one IoT sensor; and a computing device to: quantify a term of the service agreement for an IoT system in a context of a proposed solution; evaluate solution characteristics against a given gateway architecture; and compare the solution characteristics to desired solution metrics of the service agreement, wherein the solution characteristics comprise a simulated observed characteristic.

Example 17 includes the system of example 16, including or excluding optional features. In this example, the aggregation device comprises the computing device, and wherein the at least one IoT sensor comprises added IoT sensors, at least one of which is simulated.

Example 18 includes the system of any one of examples 16 to 17, including or excluding optional features. In this example, the computing device comprises a remote server.

Example 19 includes the system of any one of examples 16 to 18, including or excluding optional features. In this example, the system includes the computing device to provide a control user interface (UI) for a user to access and modify a configuration parameter. Optionally, the system includes a database accessed via the control UI, wherein the computing device comprises a processor and memory storing code executable by the processor to quantify the term, evaluate the solution characteristics, and compare the solution characteristics to the desired solution metrics.

Example 20 is a system of compliance checking. The system includes means for quantifying a term of a service agreement for an IoT system in a context of a proposed solution; means for evaluating solution characteristics against a given gateway architecture; and means for comparing the solution characteristics to desired solution metrics of the service agreement.

Example 21 includes the system of example 20, including or excluding optional features. In this example, the system includes means for providing a control user interface (UI) for a user to access and modify a configuration parameter for the IoT system. Optionally, the system includes means for controlling sensor hubs, sensors, gateways, and cloud servers. Optionally, the system includes means for initiating monitoring daemons in a device controlled by the control UI. Optionally, the system includes means for accessing a database. Optionally, the system includes means for mapping data in a tuple in the database.

Example 22 includes the system of any one of examples 20 to 21, including or excluding optional features. In this example, the system includes means for choosing configuration values for a plurality of input parameters.

Example 23 includes the system of any one of examples 20 to 22, including or excluding optional features. In this example, the system includes means for interacting defined trigger scripts, wherein the service agreement comprises a Technical Service Level Agreement (TSLA).

Example 24 is an apparatus. The apparatus includes a computing device to check compliance of a service agreement for an IoT system, comprising the computing device to: quantify a term of the service agreement in a context of a proposed solution; evaluate solution characteristics against a given gateway architecture; compare the solution characteristics to desired solution metrics of the service agreement, wherein the solution characteristics comprise a simulated observed characteristic; and provide a control user interface (UI) for a user to access and modify a configuration parameter for the IoT system.

Example 25 includes the apparatus of example 24, including or excluding optional features. In this example, the configuration parameter comprises number of sensors, sensor publish frequencies, packet sizes, burstiness of traffic profiles, or quality of service values of Message Queuing Telemetry Transport (MQTT) based transmissions, or any combinations thereof.

Example 26 includes the apparatus of any one of examples 24 to 25, including or excluding optional features. In this example, the control UI comprises an iteration generator, and wherein a user employs the iteration generator to choose configuration values for a plurality of input parameters comprising configuration parameters.

Example 27 includes the apparatus of any one of examples 24 to 26, including or excluding optional features. In this example, the control UI controls sensor hubs, sensors, a gateway, and a cloud server, and wherein to evaluate and compare comprises to employ a lookup table stored in a database.

Example 28 includes the apparatus of any one of examples 24 to 27, including or excluding optional features. In this example, the apparatus includes a database accessed via the control UI, wherein the computing device comprises a processor and memory storing code executable by the processor to quantify the term, evaluate the solution characteristics, and compare the solution characteristics to the desired solution metrics, and wherein data mapped in a tuple in the database comprises workflow configuration information, observed system performance, and resulting solution characteristics.

Example 29 includes the apparatus of any one of examples 24 to 28, including or excluding optional features. In this example, the apparatus includes application program interfaces for interaction of defined trigger scripts, wherein the service agreement comprises a Technical Service Level Agreement (TSLA).

Example 30 is a method of compliance checking. The method includes quantifying a term of a service agreement for an IoT system in a context of a proposed solution; evaluating solution characteristics against a given gateway architecture; comparing the solution characteristics to desired solution metrics of the service agreement; and accessing and modifying a configuration parameter for the IoT system via a control user interface (UI).

Example 31 includes the method of example 30, including or excluding optional features. In this example, the method includes controlling sensor hubs, sensors, gateways, and cloud servers via the control UI; and initiating monitoring daemons in a device controlled by the control UI.

Example 32 includes the method of any one of examples 30 to 31, including or excluding optional features. In this example, the method includes accessing a database via the control UI. Optionally, the method includes mapping data in a tuple in the database.

Example 33 includes the method of any one of examples 30 to 32, including or excluding optional features. In this example, the method includes choosing, via an iteration generator, configuration values for a plurality of input parameters; and interacting defined trigger scripts using application program interfaces, wherein the service agreement comprises a Technical Service Level Agreement (TSLA).

Example 34 is a tangible, non-transitory, computer-readable medium. The computer-readable medium includes instructions that direct the processor to quantify a term of a service agreement for an IoT system in a context of a proposed solution; evaluate solution characteristics against a gateway architecture; and compare the solution characteristics to desired service-agreement solution metrics.

Example 35 includes the computer-readable medium of example 34, including or excluding optional features. In this example, the computer-readable medium includes code executable by the processor to direct the processor to provide a control user interface (UI) for a user to access and modify a configuration parameter of the IoT system. Optionally, the computer-readable medium includes code executable by the processor to direct the processor to initiate monitoring daemons in a device controlled by the control UI.

Example 36 includes the computer-readable medium of any one of examples 34 to 35, including or excluding optional features. In this example, the computer-readable medium includes code comprising an iteration generator executable by a processor to direct the processor to choose configuration values for a plurality of input parameters. Optionally, the input parameters comprise configuration parameters comprising number of sensors, sensor publish frequencies, packet sizes, and burstiness of traffic profiles. Optionally, the configuration parameter comprises number of sensors, sensor publish frequencies, packet sizes, burstiness of traffic profiles, or quality of service values of Message Queuing Telemetry Transport (MQTT) based transmissions, or any combinations thereof.

Example 37 includes the computer-readable medium of any one of examples 34 to 36, including or excluding optional features. In this example, the service agreement comprises a Technical Service Level Agreement (TSLA).

Example 38 includes the computer-readable medium of any one of examples 34 to 37, including or excluding optional features. In this example, an aggregation device of the IoT system comprises the processor.

Example 39 is a computing device to check compliance of a service agreement for an IoT system. The computing device includes to quantify a term of the service agreement in a context of a proposed solution; evaluate solution characteristics against a given gateway architecture; and compare the solution characteristics to desired solution metrics of the service agreement, wherein the solution characteristics comprise a simulated observed characteristic, and wherein the service agreement comprises a Technical Service Level Agreement (TSLA).

Example 40 includes the computing device of example 39, including or excluding optional features. In this example, the computing device comprises a control user interface (UI) for a user to access and modify a configuration parameter for the IoT system. Optionally, the configuration parameter comprises number of sensors, sensor publish frequencies, packet sizes, burstiness of traffic profiles, or quality of service values of Message Queuing Telemetry Transport (MQTT) based transmissions, or any combinations thereof. Optionally, the control UI comprises an iteration generator, and wherein a user employs the iteration generator to choose configuration values for a plurality of input parameters comprising configuration parameters. Optionally, the control UI controls sensor hubs, sensors, a gateway, and a cloud server, and wherein to evaluate and compare comprises to employ a lookup table stored in a database. Optionally, the computing device includes a database accessed via the control UI, wherein the computing device comprises a processor and memory storing code executable by the processor to quantify the term, evaluate the solution characteristics, and compare the solution characteristics to the desired solution metrics. Optionally, data mapped in a tuple in the database comprises workflow configuration information, observed system performance, and resulting solution characteristics.

Example 41 includes the computing device of any one of examples 39 to 40, including or excluding optional features. In this example, the computing device includes application program interfaces for interaction of defined trigger scripts.

Example 42 is a system for compliance checking. The system includes means for quantifying a term of a service agreement for an IoT system in a context of a proposed solution; means for evaluating solution characteristics against a given gateway architecture; means for comparing the solution characteristics to desired solution metrics of the service agreement; and means for accessing and modifying a configuration parameter for the IoT system.

Example 43 includes the system of example 42, including or excluding optional features. In this example, the system includes means for controlling sensor hubs, sensors, gateways, and cloud servers.

Example 44 includes the system of any one of examples 42 to 43, including or excluding optional features. In this example, the system includes means for initiating monitoring daemons in a device controlled by a control UI.

Example 45 includes the system of any one of examples 42 to 44, including or excluding optional features. In this example, the system includes means for accessing a database. Optionally, the system includes means for mapping data in a tuple in the database.

Example 46 includes the system of any one of examples 42 to 45, including or excluding optional features. In this example, the system includes means for choosing configuration values for a plurality of input parameters.

Example 47 includes the system of any one of examples 42 to 46, including or excluding optional features. In this example, the system includes means for interacting defined trigger scripts.

Example 48 includes the system of any one of examples 42 to 47, including or excluding optional features. In this example, the service agreement comprises a Technical Service Level Agreement (TSLA).

Examples of Code

The following example code builds a service-agreement database such as a service level agreement (SLA) database. The type of programming code or language employed in this example is the Python® programming language. Other programming languages may be employed. Moreover, customer expectations are represented in terms of SLA definitions. The SLA definitions are quantified into solution characteristics. The quantified solution characteristics for the respective SLA definitions are stored in an SLA database. The SLA database provides a lookup table for determining whether an architecture satisfies or violates an SLA definition. The following code for building a database and providing a look-up table is only an example. Other code to build a database and generate a look-up table is applicable.

```
import MySQLdb as mdb
con = mdb.connect('localhost', 'SLAuser', 'SLA123', 'SLAdb');
    with con:
        cur = con.cursor( )
        cur.execute("DROP TABLE IF EXISTS SLAProfiles")
        # CPU Freq in MHz, RAM in GB, Pub Rate in seconds, CPU Usage in percent
        # Load Avg from Platform, Free Memory in MB,
        # Disk Usage in percentage, Network Usage in percentage
        cur.execute("CREATE TABLE SLAProfiles(Id INT PRIMARY KEY
AUTO_INCREMENT, \
            CPUFreq INT, RAM INT, NumSensors INT, PubRate INT, \
            BurstCount INT, CPUusage INT, LoadAvg INT, FreeMem INT, \
            DiskUse INT, NwUse INT)")
def SLA_DB_Build(freq, ram, numSensors, pubRate, burstCount, cpuUsage, ldAvg,
memFree, diskUse, nwUse):
    # Add SLA characteristics to Database like
    # CPU, Load Average, Free memory, Disk Usage, Network Use
    # with associated Gateway (CPU freq, RAM) and
    # workflow characteristics (# of sensors, publish rate, burst count)
    con = mdb.connect('localhost', 'SLAuser', 'SLA123', 'SLAdb');
    with con:
        cur = con.cursor(mdb.cursors.DictCursor)
        cur.execute("INSERT INTO SLAProfiles(CPUFreq, RAM, NumSensors, PubRate,
BurstCount, CPUusage, LoadAvg, FreeMem, DiskUse, NwUse)
VALUES({ },{ },{ },{ },{ },{ },{ },{ },{ },{ })".format(freq, ram, numSensors, pubRate, burstCount,
cpuUsage, ldAvg, memFree, diskUse, nwUse))
        con.commit( )con.commit( )
```

The following code evaluates workloads for SLA compliance. Workloads $W_i$ and the associated solution or observed characteristics $S_i$ are assigned to a given architecture $G_x$. A decision is made as to whether observed characteristics $S_i$ are less than or equal to the relevant TSLA terms $S_{SLA}$. The comparison involves the utilization of a lookup table of a database developed using the code given above. If the comparison indicates that $S_i$ satisfies the $S_{SLA}$, the $S_i$ is SLA compliant for the workload $W_i$. If the comparison indicates that $S_i$ does not satisfy the $S_{SLA}$, the $S_i$ is not SLA compliant for the workload $W_i$. The counter i is incremented. The code repeats itself until the counter i reaches a desired number n. The code below is given only as an example.

```
def SLA_DB_lookup(freq, ram, numSensors, pubRate, burstCount, cpuUsage, IdAvg,
memFree, diskUse, nwUse):
    #Lookup stored SLA characteristics with collected characteristics
    fobj = open("ircnicks.txt", 'w')
    con = mdb.connect('localhost', 'ADuser', 'AD123', 'ADdb');
    with con:
        cur = con.cursor(mdb.cursors.DictCursor)
        cur.execute("SELECT CPUusage, LoadAvg, FreeMem, DiskUse, NwUse FROM
ADProfiles WHERE CPUFreq = freq AND RAM = ram AND NumSensors = numSensors
AND PubRate = pubRate AND BurstCount = burstCount")
        rows = cur.fetchall( )
        for row in rows:
            # If the collected stats are within the stored SLA or outside, Store in a file with
appropriate tag
            if (cpuUsage <= row["CPUusage"]) and (IdAvg <= row["LoadAvg"]) and (memFree >=
row["FreeMem"] and (diskUse <= row["DiskUse"]) and (nwUse <= row["NwUse"])):
                fobj.write("SLA Complaint : ")
                fobj.write(row)
                fobj.write("\n")
            else:
                fobj.write("SLA NONComplaint : ")
                fobj.write(row)
                fobj.write("\n")
    fobj.close( )
```

Some embodiments may be implemented in one or a combination of hardware, firmware, and software. Some embodiments may also be implemented as instructions stored on the tangible, non-transitory, machine-readable medium, which may be read and executed by a computing platform to perform the operations described. In addition, a machine-readable medium may include any mechanism for storing or transmitting information in a form readable by a machine, e.g., a computer. For example, a machine-readable medium may include read only memory (ROM); random access memory (RAM); magnetic disk storage media; optical storage media; flash memory devices; or electrical, optical, acoustical or other form of propagated signals, e.g., carrier waves, infrared signals, digital signals, or the interfaces that transmit and/or receive signals, among others.

An embodiment is an implementation or example. Reference in the specification to "an embodiment," "one embodiment," "some embodiments," "various embodiments," or "other embodiments" means that a particular feature, structure, or characteristic described in connection with the embodiments is included in at least some embodiments, but not necessarily all embodiments, of the present techniques. The various appearances of "an embodiment," "one embodiment," or "some embodiments" are not necessarily all referring to the same embodiments.

Not all components, features, structures, characteristics, etc. described and illustrated herein need be included in a particular embodiment or embodiments. If the specification states a component, feature, structure, or characteristic "may", "might", "can" or "could" be included, for example, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

It is to be noted that, although some embodiments have been described in reference to particular implementations, other implementations are possible according to some embodiments. Additionally, the arrangement and/or order of circuit elements or other features illustrated in the drawings and/or described herein need not be arranged in the particular way illustrated and described. Many other arrangements are possible according to some embodiments.

In each system shown in a figure, the elements in some cases may each have a same reference number or a different reference number to suggest that the elements represented could be different and/or similar. However, an element may be flexible enough to have different implementations and work with some or all of the systems shown or described herein. The various elements shown in the figures may be the same or different. Which one is referred to as a first element and which is called a second element is arbitrary.

It is to be understood that specifics in the aforementioned examples may be used anywhere in one or more embodiments. For instance, all optional features of the computing device described above may also be implemented with respect to either of the method or the computer-readable medium described herein. Furthermore, although flow diagrams and/or state diagrams may have been used herein to describe embodiments, the techniques are not limited to those diagrams or to corresponding descriptions herein. For example, flow need not move through each illustrated box or state or in exactly the same order as illustrated and described herein.

The present techniques are not restricted to the particular details listed herein. Indeed, those skilled in the art having the benefit of this disclosure will appreciate that many other variations from the foregoing description and drawings may be made within the scope of the present techniques. Accordingly, it is the following claims including any amendments thereto that define the scope of the present techniques.

What is claimed is:

1. An apparatus comprising a computing device, comprising:
    a processor; and
    a mass storage comprising code to direct the processor to:
    check compliance of a service agreement for an IoT system, comprising code to direct the processor to:
        quantify terms of the service agreement in a context of a proposed solution;
        evaluate proposed solution characteristics of the proposed solution against a given gateway architecture by executing a list of permutations of simulated workflows against the given gateway architecture; and
        compare the proposed solution characteristics to desired solution metrics of the service agreement, wherein the proposed solution characteristics comprise a simulated observed characteristic of a service level agreement;

wherein to evaluate and compare comprises to employ a lookup table stored in a database, and the lookup table helps contain a number of executions by only allowing permutations that are compliant.

2. The apparatus of claim 1, wherein the computing device comprises a control user interface (UI) for a user to access and modify a configuration parameter for the IoT system.

3. The apparatus of claim 2, wherein the configuration parameter comprises at least one of number of sensors, sensor publish frequencies, packet sizes, burstiness of traffic profiles, or quality of service values of Message Queuing Telemetry Transport (MQTT) based transmissions.

4. The apparatus of claim 2, wherein the control UI controls sensor hubs, sensors, a gateway, and a cloud server, and wherein the control UI comprises an iteration generator, and wherein a user employs the iteration generator to choose configuration values for a plurality of input parameters comprising configuration parameters.

5. The apparatus of claim 2, comprising a database accessed via the control UI, wherein data mapped in a tuple in the database comprises workflow configuration information, observed system performance, and resulting solution characteristics, and wherein the computing device comprises a processor and memory storing code executable by the processor to quantify the term, evaluate the solution characteristics, and compare the solution characteristics to the desired solution metrics.

6. The apparatus of claim 1, wherein the context comprises a factor under which the term was quantified.

7. The apparatus of claim 1, wherein the given gateway architecture is a hybrid comprising live and simulated components.

8. A method of compliance checking, comprising:
quantifying terms of a service agreement for an IoT system in a context of a proposed solution;
simulating proposed solution characteristics of the proposed solution for a given gateway architecture by executing a list of permutations of simulated workflows against the given gateway architecture; and
comparing the proposed solution characteristics to desired solution metrics of the service agreement, wherein the proposed solution characteristics comprise a simulated observed characteristic of the service agreement;
wherein simulating and comparing comprises to employ a lookup table stored in a database, and the lookup table helps contain a number of executions by only allowing permutations that are compliant.

9. The method of claim 8, wherein the context comprises a factor under which a parameter is measured.

10. The method of claim 8, wherein the given gateway architecture comprises a hybrid of real and simulated components.

11. The method of claim 8, comprising:
accessing and modifying a configuration parameter for the IoT system via a control user interface (UI);
controlling sensor hubs, sensors, gateways, and cloud servers via the control UI; and
initiating monitoring daemons in a device controlled by the control UI.

12. The method of claim 11, comprising:
accessing a database via the control UI; and
mapping data in a tuple in the database.

13. The method of claim 8, comprising choosing, via an iteration generator, configuration values for a plurality of input parameters.

14. The method of claim 8, comprising interacting defined trigger scripts via application program interfaces, wherein the service agreement comprises a Technical Service Level Agreement (TSLA).

15. A tangible, non-transitory, computer-readable medium comprising code executable by a processor to direct the processor to:
quantify terms of a service agreement for an IoT system in a context of a proposed solution;
simulate proposed solution characteristics of the proposed solution against a given gateway architecture by executing a list of permutations of simulated workflows against the given gateway architecture; and
compare the proposed solution characteristics to desired service-agreement solution metrics, wherein the proposed solution characteristics comprise a simulated observed characteristic of the service agreement;
wherein to simulate and compare comprises to employ a lookup table stored in a database, and the lookup table helps contain a number of executions by only allowing permutations that are compliant.

16. The tangible, non-transitory, computer-readable medium of claim 15, comprising code executable by the processor to direct the processor to provide a control user interface (UI) for a user to access and modify a configuration parameter of the IoT system.

17. The tangible, non-transitory, computer-readable medium of claim 16, comprising code executable by the processor to direct the processor to initiate monitoring daemons in a device controlled by the control UI.

18. The tangible, non-transitory, computer-readable medium of claim 15, comprising code comprising an iteration generator executable by a processor to direct the processor to choose configuration values for a plurality of input parameters.

19. The tangible, non-transitory, computer-readable medium of claim 15, wherein the context comprises a factor under which the term was quantified.

20. The tangible, non-transitory, computer-readable medium of claim 15, wherein the given gateway architecture is a hybrid comprising live and simulated components.

21. An IoT system, comprising:
an aggregation device;
at least one IoT sensor; and
a computing device comprising:
a processor; and
a mass storage comprising instructions that when executed by the processor, direct the processor to:
quantify terms of the service agreement for an IoT system in a context of a proposed solution;
simulate proposed solution characteristics of the proposed solution against a given gateway architecture by executing a list of permutations of simulated workflows against the given gateway architecture; and
compare the proposed solution characteristics to desired solution metrics of the service agreement, wherein the proposed solution characteristics comprise a simulated observed characteristic of the service agreement;
wherein to simulate and compare comprises to employ a lookup table stored in a database, and the lookup table helps contain a number of executions by only allowing permutations that are compliant.

22. The IoT system of claim 21, wherein the aggregation device comprises the computing device, and wherein the at least one IoT sensor comprises added IoT sensors, at least one of which is simulated.

23. The IoT system of claim 21, wherein the computing device comprises a remote server.

24. The IoT system of claim 21, wherein the mass storage comprises code to direct the processor to provide a control user interface (UI) for a user to access and modify a configuration parameter.

25. The IoT system of claim 24, comprising a database accessed via the control UI, wherein the computing device comprises a processor and memory storing code executable by the processor to quantify the term, evaluate the solution characteristics, and compare the solution characteristics to the desired solution metrics.

\* \* \* \* \*